US009775567B2

(12) United States Patent
Suchecki et al.

(10) Patent No.: US 9,775,567 B2
(45) Date of Patent: *Oct. 3, 2017

(54) INTRAVASCULAR SENSING METHOD AND SYSTEM

(71) Applicant: ACIST MEDICAL SYSTEMS, INC., Eden Prairie, MN (US)

(72) Inventors: Todd M. Suchecki, Robbinsdale, MN (US); Alan K. Evans, Otsego, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/978,835

(22) Filed: Dec. 22, 2015

(65) Prior Publication Data

US 2016/0106373 A1    Apr. 21, 2016

Related U.S. Application Data

(63) Continuation of application No. 13/469,485, filed on May 11, 2012, now Pat. No. 9,259,161.
(Continued)

(51) Int. Cl.
*A61B 5/02* (2006.01)
*A61B 5/00* (2006.01)
(Continued)

(52) U.S. Cl.
CPC ............ *A61B 5/7221* (2013.01); *A61B 5/026* (2013.01); *A61B 5/02007* (2013.01);
(Continued)

(58) Field of Classification Search
None
See application file for complete search history.

(56) References Cited

U.S. PATENT DOCUMENTS

| 4,006,735 A | 2/1977 | Hittman et al. |
| 4,771,782 A | 9/1988 | Millar et al. |

(Continued)

FOREIGN PATENT DOCUMENTS

| CN | 1829466 A | 9/2006 |
| EP | 1419796 B1 | 3/2008 |

(Continued)

OTHER PUBLICATIONS

FISO Technologies, Inc., Brochure (Product Data Sheet) for "FOP-MIV Pressure Sensor," downloaded from http://www.fiso.com on Aug. 29, 2008, 2 pages.

(Continued)

*Primary Examiner* — Etsub Berhanu
(74) *Attorney, Agent, or Firm* — Fredrikson & Byron, P.A.

(57) ABSTRACT

Described herein are methods and systems for calculating a corrected Fractional Flow Reserve (FFR). An illustrative method includes delivering a first pressure sensing device including a pressure sensor to a location in a blood vessel having a stenosis, positioning the pressure sensor distal to the stenosis, measuring the distal pressure, measuring the proximal pressure, and calculating a corrected FFR using the measured proximal and distal pressures and applying a correction factor or correction equation. The corrected FFR may approximate a FFR that would have been obtained if the pressure measured downstream of the stenosis was measured using a second pressure sensing device having a second maximum cross-sectional area in a distal portion of the second pressure sensing device that is different from the first maximum cross-sectional area.

20 Claims, 29 Drawing Sheets

Related U.S. Application Data

(60) Provisional application No. 61/484,929, filed on May 11, 2011.

(51) Int. Cl.
*A61B 5/0215* (2006.01)
*A61B 5/026* (2006.01)
*A61M 25/00* (2006.01)

(52) U.S. Cl.
CPC ........ *A61B 5/0215* (2013.01); *A61B 5/02158* (2013.01); *A61B 5/6851* (2013.01); *A61B 5/0066* (2013.01); *A61B 5/4842* (2013.01); *A61M 2025/0002* (2013.01)

(56) References Cited

U.S. PATENT DOCUMENTS

| | | |
|---|---|---|
| 4,850,358 A | 7/1989 | Millar et al. |
| 4,901,731 A | 2/1990 | Millar |
| 4,928,693 A | 5/1990 | Goodin et al. |
| 4,966,148 A | 10/1990 | Millar et al. |
| 4,991,590 A | 2/1991 | Shi |
| 5,046,497 A | 9/1991 | Millar et al. |
| 5,178,159 A | 1/1993 | Christian |
| 5,280,786 A | 1/1994 | Wlodarczyk et al. |
| 5,395,311 A | 3/1995 | Andrews |
| 5,533,957 A | 7/1996 | Aldea |
| 5,597,377 A | 1/1997 | Aldea |
| 5,715,827 A | 2/1998 | Corl et al. |
| 5,782,797 A | 7/1998 | Schweich et al. |
| 5,800,397 A | 9/1998 | Wilson et al. |
| 5,938,624 A | 8/1999 | Akerfeldt et al. |
| 6,112,598 A | 9/2000 | Tenerz et al. |
| 6,146,354 A | 11/2000 | Beil |
| 6,166,806 A | 12/2000 | Tjin |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,295,990 B1 | 10/2001 | Lewis et al. |
| 6,471,656 B1 | 10/2002 | Shalman et al. |
| 6,615,667 B2 | 9/2003 | Smith |
| 6,733,459 B1 | 5/2004 | Atsumi |
| 6,852,261 B2 | 2/2005 | Benjamin |
| 6,868,736 B2 | 3/2005 | Sawatari et al. |
| 6,976,965 B2 | 12/2005 | Corl et al. |
| 7,134,994 B2 | 11/2006 | Alpert et al. |
| 7,329,223 B1 | 2/2008 | Ainsworth et al. |
| 7,458,938 B2 | 12/2008 | Patel et al. |
| 7,507,237 B2 | 3/2009 | Geistert |
| 8,298,156 B2 | 10/2012 | Manstrom et al. |
| 2002/0072647 A1 | 6/2002 | Schock et al. |
| 2002/0072679 A1 | 6/2002 | Schock et al. |
| 2003/0216621 A1 | 11/2003 | Alpert et al. |
| 2004/0168519 A1 | 9/2004 | Kalvensten et al. |
| 2005/0065511 A1 | 3/2005 | Geistert |
| 2005/0234428 A1 | 10/2005 | Spohn et al. |
| 2006/0133715 A1 | 6/2006 | Belleville et al. |
| 2007/0255145 A1 | 11/2007 | Smith et al. |
| 2008/0119758 A1 | 5/2008 | Samuelsson et al. |
| 2010/0234698 A1 | 9/2010 | Manstrom et al. |
| 2010/0241008 A1 | 9/2010 | Belleville et al. |
| 2013/0190633 A1 | 7/2013 | Dorando et al. |
| 2014/0024950 A1 | 1/2014 | Hiltner et al. |
| 2015/0133799 A1 | 5/2015 | O'Connell et al. |

FOREIGN PATENT DOCUMENTS

| | | |
|---|---|---|
| JP | H03-32640 A | 2/1991 |
| JP | H03-505822 A | 12/1991 |
| JP | H11-188010 A | 7/1999 |
| JP | H11-244248 A | 9/1999 |
| JP | 2000504249 A | 4/2000 |
| JP | 2002513605 A | 5/2002 |
| JP | 2003525067 A | 8/2003 |
| JP | 2004528920 A | 9/2004 |
| JP | 2004357985 A | 12/2004 |
| JP | 2005131421 A | 5/2005 |
| JP | 2005270425 A | 10/2005 |
| JP | 2005291945 A | 10/2005 |
| JP | 2006509547 A | 3/2006 |
| JP | 2008514308 A | 5/2008 |
| JP | 2012501807 A | 1/2012 |
| RU | 1802695 A3 | 3/1993 |
| RU | 47203 U1 | 8/2005 |
| WO | 2010030882 A1 | 3/2010 |
| WO | 2011161212 A1 | 12/2011 |

OTHER PUBLICATIONS

Li et al., "Optical MEMS pressure sensor based on Fabry-Perot interferometry," Optics Express, Feb. 20, 2006, pp. 1497-1504.
Opsens Inc., Brochure (Product Data Sheet) entitled, "Fiber Optic Miniature Physiological Pressure Sensor OPP-M, MEMS-based Fiber Optic Pressure Sensor for Life Science Applications," downloaded from http://www. opsens.com on Aug. 29, 2008, 2 pages.
Sauser et al., "Pressure Microsensing Catheters for Neonatal Care," Proceedings of IEEE Sensors, 3, Art. No. W3L-A.1, 2004, pp. 1476-1479.
Serruys, MD, PhD et al., "Intracoronary Pressure and Flow Velocity with Sensor-Tip Guidewires: A New Methodological Approach for Assessment of Coronary Hemodynamics Before and After Coronary Interventions," The American Journal of Cardiology, vol. 71, No. 14, May 20, 1993, pp. D41-D53.
Tabbara et al., "Potential of intraluminal ultrasound for antioplasty guidance," Proceedings of SPIE—The International Society for Optical Engineering, 1201, 1990, pp. 523-526.
Gould et al. "Experimental Validation of Quantitative Coronary Arteriography for Determining Pressure-Flow Characteristics of Coronary Stenosis" Circulation, vol. 66, No. 5, Nov. 1982, pp. 930-937.
Ashtekar et al. "In vitro quantification of guidewire flow-obstruction effect in model coronary stenoses for interventional diagnostic procedure", Journal of Medical Devices, vol. 1, Sep. 2007, pp. 185-196, XP002683319.
A. S. Roy et al. "Delineating the guide-wire flow obstruction effect in assessment of fractional flow reserve and coronary flow reserve measurements", AJP: Heart and Circulatory Physiology, vol. 289, No. 1, Jul. 1, 2005, pp. H392-H397, XP55038025, ISSN: 0363-6135, DOI: 10. 1152/ajpheart 00798.2004 abstract.
A.S. Roy et al. "Guidewire flow obstruction effect on pressure drop-flow relationship in moderate coronary artery stenosis", Journal of Biomechanics, Pergamon Press, New York, NY, vol. 39, No. 5, Jan. 1, 2006, pp. 853-864, X024980159, ISSN: 0021-9290, DOI: 10.1016/J.Jbiomech. 2005.01.020.
Pijis et al., "Measurement of Fractional Flow Reserve to Assess the Functional Severity of Coronary-Artery Stenoses", The New England Journal of Medicine, Sep. 12, 2008, pp. 1703-1708.
International Search Report and Written Opinion, dated Feb. 10, 2012 for PCT Application No. PCT/US12/037503, 13 pages.
English Machine Translation of Japanese Publication No. JP2012501807, Publication Date: Jan. 26, 2012, 69 pages.
English Translation of Abstract of Japanese Publication No. JP2003525067, Publication Date: Aug. 26, 2003, 1 page.

INTRAVASCULAR SENSING METHOD AND SYSTEM

PRIORITY

This application is a continuation application of U.S. patent application Ser. No. 13/469,485, filed May 11, 2012, entitled Intravascular Sensing Method and System, which application claims priority to U.S. Provisional Application Ser. No. 61/484,929, entitled Intravascular Sensing Method and System and filed May 11, 2011, the disclosures of which are hereby incorporated by reference in their entirety.

TECHNICAL FIELD

This application relates generally to the field of medical device technology and, more particularly, to devices and methods for positioning and utilizing physiological sensors in anatomical (e.g., vascular) structures of patients, such as in blood vessels.

BACKGROUND

Stenosis of a blood vessel causes narrowing of the vessel at the location of the stenosis. This narrowing effects blood flow and, if further blockage occurs, can cause damage to tissues supplied by the vessel. For example, when stenosis occurs in a coronary artery, the blood supply to the portion of the heart supplied by that artery may be compromised. If the stenosis is severe, there is an increased risk of myocardial infarction.

Various methods are known to measure the degree of obstruction caused by a stenotic lesion in a vessel. Some methods rely on visual observation during the injection of contrast media. A more precise evaluation can be made by directly or indirectly measuring the flow of blood across the lesion. Such measurements may then be used to determine whether or not the degree of stenosis is sufficiently severe that intervention is warranted, and what that intervention should be.

One measurement of the severity of stenosis in a blood vessel is the Fractional Flow Reserve, or FFR, which is calculated based on pressure measurements. To calculate the FFR for a given stenosis, two blood pressure readings are taken. One pressure reading is taken on the distal side of the stenosis (e.g., downstream from the stenosis), the other pressure reading is taken on the proximal side of the stenosis (e.g., upstream from the stenosis and closer to the aorta). The FFR is defined as the ratio of maximal blood flow in a stenotic artery, taken distal to the lesion, to normal maximal flow, and is typically calculated based on a measured pressure gradient of the distal pressure to the proximal pressure. The FFR is therefore a unitless ratio of the distal and proximal pressures. The pressure gradient, or pressure drop, across a stenotic lesion is an indicator of the severity of the stenosis, and the FFR is a useful tool in assessing the pressure drop. The more restrictive the stenosis is, the greater the pressure drop, and the lower the resulting FFR.

The FFR measurement may be a useful diagnostic and treatment planning tool. For example, clinical studies have shown that an FFR of less than about 0.75 may be a useful criterion on which to base certain therapy decisions. An example of such a study is Pijls, DeBruyne et al., Measurement of Fractional Flow Reserve to Assess the Functional Severity of Coronary-Artery Stenoses, 334:1703-1708, New England Journal of Medicine, Jun. 27, 1996. A physician might decide, for example, to perform an interventional procedure (e.g., angioplasty or stent placement) when the FFR for a given stenotic lesion is below 0.75, and may decide to forego such treatment for lesions where the FFR is above 0.75. In other studies, the cut off value for the FFR at which an intervention is performed is 0.80. Thus, the FFR measurement can provide a decision point for guiding treatment decisions.

One method of measuring blood pressure for use in calculating FFR is to use a pressure sensing guidewire. Such a device has a pressure sensor embedded within the guidewire itself. A pressure sensing guidewire could be used in the deployment of interventional devices such as angioplasty balloons or stents. To use a pressure sensing guidewire, in certain applications the guidewire must be repositioned so the sensing element of the guidewire is correctly placed with respect to a stenotic lesion, for example. Blood pressure measurements for calculating FFR, for example, are generally taken on both sides of a given stenosis, and one way in which the upstream measurement could be made would be to retract the guidewire across the stenosis to make the upstream measurement. The guidewire may also be retracted across the stenosis in order to normalize the pressure sensor to an aortic pressure. After retracting the guidewire to make the proximal pressure measurement or to normalize the pressure, the guidewire may again be repositioned downstream of the lesion, for example, if it is determined (e.g., based on the FFR calculation) that an interventional device should be deployed. In cases where there are multiple lesions, if the guidewire is used to make a proximal pressure measurement, the sensing element of a pressure sensing guidewire would need to be advanced and retracted across multiple lesions, and would potentially have to be advanced and repositioned again for each such lesion. Advancing and maneuvering a pressure sensing guidewire though stenotic lesions and the vasculature, for example, can be a difficult and/or time consuming task.

Physician preference is another factor that may influence the choice of diagnostic tools or techniques used for certain applications. For example, some physicians may tend to become accustomed to using certain specific guidewires for certain applications. "Standard" (e.g., commercially available) medical guidewires may vary in size, flexibility, and torque characteristics. A physician may prefer to use different guidewires for different tasks, for example, to access hard-to-reach anatomical areas, or when encountering bifurcations in arteries. Certain guidewires may therefore be better suited for specific tasks because of the torque and flexing characteristics, and a physician may display a strong preference for using a certain guidewire based on the specific task (or tasks) he or she is facing. A pressure sensing guidewire may have torque and flexing characteristics that are either unknown to the physician, or that are unsuitable for a particular task, because such a guidewire is specifically constructed to have a pressure sensor incorporated as part of the guidewire itself. As a result, a physician may find it difficult to maneuver a pressure sensing guidewire into an anatomical location of interest, as compared to a "standard" (e.g., non-pressure sensing) medical guidewire.

Having grown accustomed to the handling characteristics of a particular standard, non-pressure sensing guidewire, a physician may be reluctant to employ a pressure sensing guidewire, which may increase the time and difficulty of positioning and repositioning the pressure sensing guidewire across a stenotic lesion, for example. In such cases, a physician may choose to forego the benefit of a diagnostic measurement, such as FFR, and simply choose to deploy some form of interventional therapy as a conservative approach to such decisions. If the diagnostic measurement techniques and the associated devices were simple enough to use, more physicians would use them and thereby make better therapy decisions.

It should also be noted that when pressure measurements are made using a pressure sensing guidewire, some error may be introduced due to the cross sectional size of the guidewire, which typically has an outer diameter of about 0.014 inches. This is because, as the guidewire crosses the lesion, the guidewire itself introduces blockage, in addition to that caused by the lesion itself. The measured distal pressure is therefore somewhat lower than it would be without the additional flow obstruction caused by the guidewire. The presence of the guidewire within the artery may therefore exaggerate the measured pressure gradient across the lesion. Nevertheless, many clinical studies evaluating FFR, which are used to determine the FFR at which various interventions should be employed, use pressure sensing guidewires to measure and calculate the FFR cutoff. As such, the values determined in these clinical studies are offset from the true FFR by the amount of the error caused by the presence of the pressure sensing guidewire. However, measurements obtained using this method do not necessarily need to be corrected for this error, since the values against which they are compared for making treatment decisions (the values based on clinical studies) also include this error if they are obtained in the same way (that is, using a pressure sensing guidewire). Therefore treatment decisions may be made using the FFR obtained using a pressure sensing guidewire without correcting for the error caused by the presence of the guidewire.

SUMMARY

Embodiments of the invention include systems and methods for determining a corrected pressure measurement such as a corrected FFR by applying a correction factor or a correction equation to blood pressure measurements or FFR values obtained using a pressure sensing device in a vascular structure of a patient. For example, in some embodiments, the system includes a sensor, such as a sensor delivery device or a guidewire sensor, and a processor. The sensor delivery device may include a distal sleeve having an outer diameter and a guidewire lumen for slidably receiving a guidewire, a blood pressure sensor coupled to the distal sleeve, and a proximal portion coupled to the distal sleeve including a communication channel for communicating a blood pressure measurement from the sensor to the processor. The processor may be configured to receive the blood pressure measurement and to calculate a corrected FFR using the blood pressure measurement and a correction factor or correction equation, wherein the correction factor or correction equation vary depending upon the maximum outer diameter of the device in the portion of the device crossing the stenosis and/or patient physiology (such as vessel size and/or lesion size). In some embodiments, some or all of the system may be a part of a fluid injector system.

Some embodiments include methods of calculating a corrected Fractional Flow Reserve including delivering a pressure sensing device including a pressure sensor to a location in an artery having a stenosis, positioning the pressure sensor distal to the stenosis, measuring a pressure distal to the stenosis while the pressure sensor is positioned distal to the stenosis, measuring a pressure proximal to the stenosis, and calculating a corrected Fractional Flow Reserve using the measured proximal and distal pressures and applying a correction factor or correction equation. The correction factor or correction equation may correct for changes in the measured distal pressure caused by a presence of the pressure sensing device.

In some embodiments, the method also includes selecting the correction factor or correction equation from a group of at least two correction factors or correction equations. The selection of the correction factor or correction equation may be determined by the maximum cross-sectional area of the portion of the pressure sensing device crossing the stenosis during the step of measuring the distal pressure or alternatively by the type or identity of the pressure sensing device. The selection of the correction factor or correction equation may also be determined by the size of the stenosis, the size of the lumen of the artery, and/or the rate of blood flow and in some embodiments the pressure sensing device also includes one or more sensors to measure these variables.

The corrected Fractional Flow Reserve approximates a Fractional Flow Reserve that would be obtained if the distal pressure was measured differently, such as by using a different device having a different maximum cross-sectional area in the portion of the different device that crosses the stenosis while measuring the distal pressure or if no device was present crossing the stenosis. For example, the corrected Fractional Flow Reserve might approximate the Fractional Flow Reserve that would be obtained if the distal pressure was measured with a pressure sensing guidewire or with a pressure sensing device having an outer diameter of about 0.014 inches. The corrected Fractional Flow Reserve may be provided on a visual display.

The correction of the Fractional Flow Reserve may be performed in various ways. Some embodiments include multiplying the measured distal pressure by a correction factor to calculate a corrected distal pressure and calculating the corrected Fractional Flow Reserve using the corrected distal pressure. Some embodiments include applying a correction equation to the calculated Fractional Flow Reserve to obtain a corrected Fractional Flow Reserve.

Embodiments include systems for calculating a corrected Fractional Flow Reserve associated with a stenosis in an artery including a pressure sensing device configured for placement within an artery to measure pressure distal to the stenosis, a processing device in communication with the pressure sensing device, and a data set. The data set may include a group of at least two correction factors or correction equations, with each correction factor or correction equation corresponding to the maximum cross-sectional area of the portion of a standard pressure sensing device that crosses a stenosis when measuring a distal pressure or to an identity of a standard pressure sensing device. The data set may be stored within a memory component of the processing device or within a memory component accessible by the processing device. The processing device may be configured to select a correction factor or correction equation based upon the maximum cross-sectional area of the portion of the pressure sensing device of the system which crosses the stenosis when measuring a pressure distal to the stenosis or may be based on the identity of the pressure sensing device of the system. The processing device may be further configured to calculate a corrected Fractional Flow Reserve using the selected correction factor or correction equation and pressure data received from the pressure sensing device. In some embodiments, the corrected Fractional Flow Reserve approximates the Fractional Flow Reserve that would have been obtained if the pressure data was obtained using a different device with a maximum outer diameter of about 0.014 inches in the portion of the different device that would cross the stenosis while the different device measured the distal pressure.

DESCRIPTION

Various exemplary embodiments are described herein with reference to the accompanying drawing figures in which like numbers describe like elements.

Embodiments of the invention employ a pressure sensing device such as a guidewire sensor or a sensor delivery device which can be delivered on a guidewire to a location distal to a lesion, such as a stenosis in an artery, to measure pressure. Because the pressure sensor itself, and the sensor delivery device of which it is a part, have a cross sectional area which can cause some error in the distal pressure reading, embodiments of the invention correct for such error to obtain corrected distal pressure measurements, corrected pressure differences, and corrected FFRs. Furthermore, because the maximum cross sectional area of the pressure sensing device may be greater than that of the traditional 0.014 inch pressure sensing guidewires upon which the clinical values for intervention have been determined, embodiments of the invention can correct the measured FFR to approximate the FFR measurement which would have been obtained if a 0.014 inch pressure sensing guidewire were used. The FFR may alternatively be corrected to approximate the FFR measurement which would be obtained if no measuring device was used, or if a pressure measuring device of any size were used.

The size of the sensor delivery device or pressure sensing guidewire as used herein generally refers to the maximum cross-sectional area of the device or guidewire, in that portion of the device or guidewire that is positioned across the lesion when the distal pressure is measured. That is, it is the cross-sectional area (taken perpendicular to the longitudinal axis) of the device or guidewire which is the greatest, in the distal portion of the device where the device crosses the lesion and where the size of the device influences the distal pressure measurements. In embodiments in which the device has a circular cross-section, the size may also be referred to by the outer diameter, since this value correlates to the cross-sectional area.

Sensor delivery devices and methods of using sensor delivery devices which may be used in embodiments of the invention are described in U.S. Pat. Pub. No. 2010/0234698, the disclosure of which is hereby incorporated by reference in its entirety. Other types of sensor delivery devices, which may also be referred to as over the wire devices, may also be used such as the Metricath Libra®, a pressure sensing catheter available from Medical Ventures Corp. (Richmond, British Columbia). Alternatively, pressure sensing guidewires may be used, such as pressure sensing guidewires having an outer diameter greater than or less than 0.014 inches. Other catheter based intraluminal pressure sensing devices may also be used.

Figure 1:
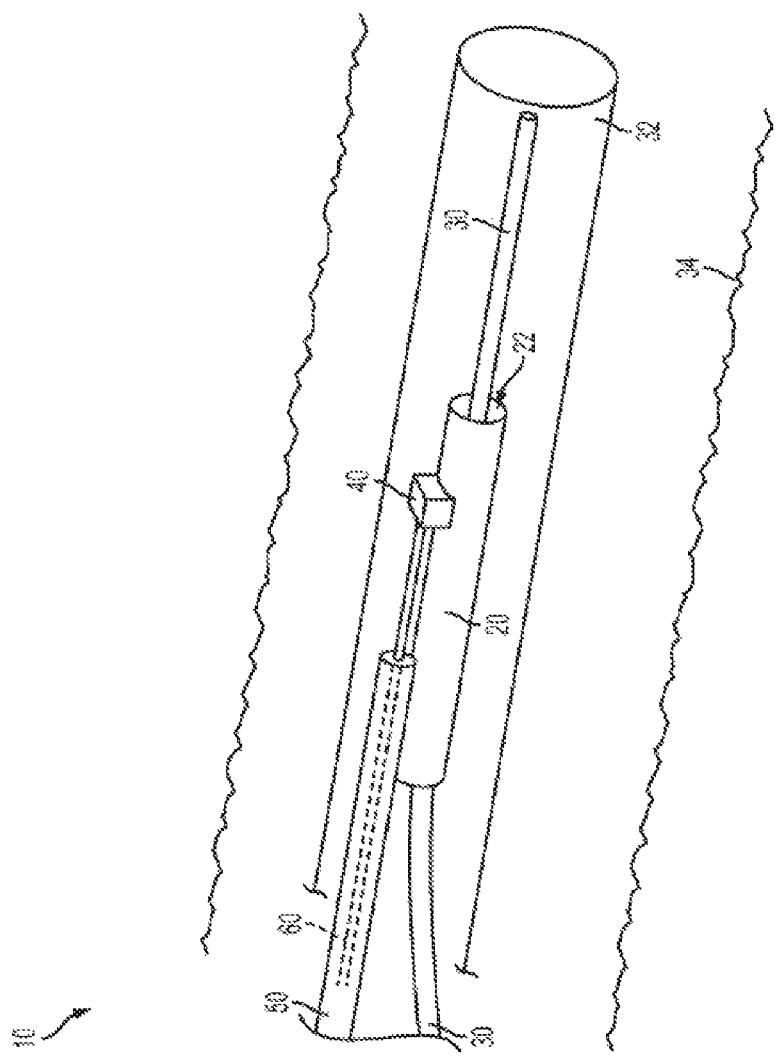
FIG. 1 is a perspective view of a sensor delivery device according to embodiments of the invention.

One embodiment of a sensor delivery device which can be used in embodiments of the invention is shown in FIG. 1. The sensor delivery device 10 of FIG. 1 includes a distal sleeve 20 having a guidewire lumen 22 extending therethrough for slidably receiving a medical guidewire 30. A sensor 40 is coupled to the distal sleeve 20, sensor 40 being capable of sensing and/or measuring a physiological parameter of a patient such as fluid pressure and generating a signal representative of the physiological parameter. Thus, the distal sleeve 20, and hence, the sensor 40, may be positioned within a patient (e.g., within an anatomical structure of a patient, such as within a vein, artery, or other blood vessel, or across a heart valve, for example) by causing the distal sleeve 20 to slide over the medical guidewire 30 to the desired position.

The delivery device 10 of FIG. 1 includes a proximal portion 50, which is coupled to the distal sleeve 20. The proximal portion 50 includes a communication channel 60 for communicating the signal from the sensor 40 to a location outside of the patient (e.g., to a processor, display, computer, monitor, or to another medical device). Communication channel 60 may comprise a fiber optic communication channel in certain preferred embodiments, such as where the sensor 40 is a fiber optic pressure sensor. Alternately, communication channel 60 may comprise an electrically conductive medium, such as one or more electrical conducting wires. Of course, many other forms of communication media may be suitable for transmitting the signal generated by sensor 40 to a location outside of the patient. In some embodiments of the invention, the communication channel 60 may comprise any of a variety of fluid and/or non-fluid communication media, such as a wireless communication link, or an infrared capability, or acoustic communications such as ultrasound, as possible examples.

The proximal portion 50 is also adapted to assist an operator (e.g., a physician or other medical staff) in positioning the distal sleeve 20 and the sensor 40 within an anatomical (e.g., vascular) structure of the patient. This is typically accomplished by an operator first inserting a "standard" medical guidewire 30 into a patient's vasculature and advancing it past an area of interest. The sensor delivery device 10 is then deployed by "threading" the distal sleeve 20 onto the guidewire 30 such that the lumen 22 slides over the guidewire 30, and advancing the distal sleeve 20 (and the associated sensor 40) by moving (e.g., pushing and/or pulling) the proximal portion 50 until sensor 40 is in the desired location.

The device 10 and the guidewire 30 are typically manipulated inside a guiding catheter 32, which has been placed in the anatomical (e.g., vascular) structure of interest. In some embodiments, the location of interest is a stenotic lesion in a coronary artery. In certain preferred embodiments of the invention, the guidewire lumen 22 may be sized to slide over "standard" sized medical guidewires. For example, a number of manufacturers make medical guidewires that range in size from less than about 0.014 inches outer diameter to more than about 0.038 inches outer diameter, typically having a finite number of common sizes within this range. "Standard" size medical guidewires might, for example, have outer diameters of 0.010, 0.014, 0.018, 0.021, 0.025, 0.028, 0.032, 0.035, and 0.038 inches. Thus, in certain preferred embodiments of the invention, the guidewire lumen 22 may be sized appropriately to accommodate a particular standard size medical guidewire sliding within the lumen. A device according to preferred embodiments of the invention may therefore be made available in a range of sizes corresponding to standard medical guidewire sizes.

In certain embodiments of the invention, the distal sleeve 20 of the device may be substantially concentric with the guidewire 30. The coupling of the proximal portion 50 to the distal sleeve 20 allows the guidewire 30 to separate from the rest of device 10 (e.g., in what is sometimes referred to as a "monorail" catheter configuration); this would typically occur inside the guiding catheter 32. The guidewire 30 and device 10 would both exit the patient at the proximal end of the guiding catheter 32 as separate devices. Having the device 10 and guidewire 30 separate allows the physician to independently control device 10 and guidewire 30, as necessary. It may also allow a physician to use a shorter guidewire for catheter exchange. Having the device 10 and guidewire 30 separate (except at the distal sleeve 20) may also result in less friction (e.g., within the guiding catheter 32) than if the device 10 and guidewire 30 had to be moved together as a unit. In some embodiments, a hydrophilic coating may be applied to various portions of the device to further reduce the amount of friction encountered, for example, when advancing or retracting device 10.

Figure 2:
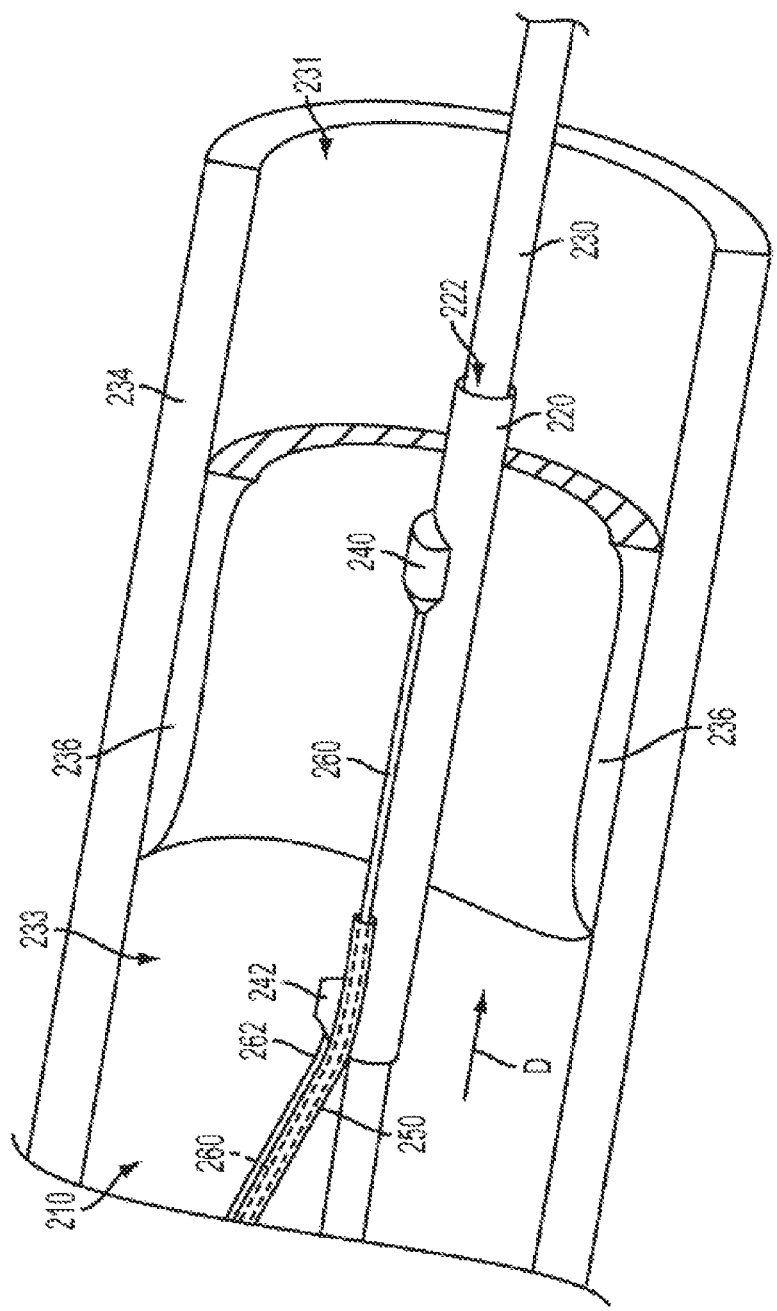
FIG. 2 is a perspective view of a sensor delivery device for making physiological measurements according to an embodiment of the invention.

FIG. 2 is a perspective view of a sensor delivery device for measuring a physiological parameter such as pressure in a patient according to an embodiment of the invention. The embodiment shown in FIG. 2 might, for example, be deployed to make an FFR measurement in a blood vessel of a patient. FIG. 2 shows a sensor delivery device 210 being deployed on a guidewire 230 in a blood vessel of a patient (e.g., coronary artery 234) across a stenosis (e.g., stenotic lesion 236). To make an FFR measurement, for example, first sensor 240 may be positioned to measure distal (downstream) blood pressure, $P_d$, at a location 231 downstream of a location of interest (e.g., stenotic lesion 236). First sensor 240 may then be positioned to measure proximal (upstream) blood pressure, $P_p$, at a location 233 upstream of a location of interest (e.g., stenotic lesion 236). FFR is simply calculated as the ratio of distal pressure to proximal pressure, or FFR=$(P_d/P_p)$. The use of the terms "downstream" or "distal" and "upstream" or "proximal" are with respect to the normal direction of blood flow, "D," as shown in FIG. 2.

In FIG. 2, first sensor 240 is coupled to distal sleeve 220. In the embodiment shown in FIG. 2, first sensor 240 is coupled to an outer surface of distal sleeve 220. The first sensor 240 is adapted to measure a physiological parameter of a patient, such as a blood pressure, and generate a signal representative of the physiological parameter. A pressure sensing range from about −50 mm Hg to about +300 mm Hg (relative to atmospheric pressure) may be desired for making most physiological measurements with sensor 240, for example.

FIG. 2 shows proximal portion 250 coupled to the distal sleeve 220. The proximal portion 250 includes a communication channel 260 for communicating the physiological parameter such as the pressure signal from the sensor 240 to a location outside of the patient (e.g., to a processor, display, computer, monitor, or to another medical device). The proximal portion 250 may preferably be formed of a material of sufficient stiffness in order to assist an operator (e.g., a physician or other medical staff) in positioning the distal sleeve 220 and the sensor 240 within an anatomical (e.g., vascular) structure of the patient.

FIG. 2 also shows an optional embodiment of the invention in which a second sensor 242 may be coupled to the device 210. For example, a second sensor 242 may be coupled to proximal portion 250 such that the first and second sensor 240, 242 are spaced apart sufficiently (e.g., a fixed distance apart) to span a stenotic lesion. This embodiment may offer the ability to measure FFR without having to reposition device 210, since first sensor 240 could be placed distal of the stenotic lesion 236 to measure $P_d$, and second sensor 242 could be placed proximal of the stenotic lesion 236 to measure $P_p$. Second sensor 242 may have a communication channel 262, which could be housed within proximal portion 250, or could be disposed along an outside surface of proximal portion 250, as shown in FIG. 2, for example.

It should be noted that certain embodiments could have more than 2 sensors, and that the spacing between adjacent sensors in such embodiments may be varied to provide a variable spacing capability. Other variations of a sensor delivery device as described in U.S. Pat. Pub. No. 2010/0234698 are also contemplated for use in embodiments of the invention. In addition, one or more additional sensors may be located on the distal end of the pressure sensing device, such as on the distal sleeve 220, for measuring physiological parameters in the vessel environment such as the vessel size (such as the inner diameter and/or cross-sectional area of the vessel lumen), lesion size (such as lesion length or minimum inner diameter or cross sectional area within the lesion, or lesion shape), blood flow rate, and temperature. In some embodiments, one or more sensors may measure the size of the lesion and/or the vessel using ultrasound (such as IVUS), impedance, or optical coherence tomography (OCT). When additional sensors are used, they may each include a communication channel, like channel 260, which may extend along or within the proximal portion 250 to a location outside of the patient, or may use other forms of communication as described herein such as wireless communication.

Figure 3:
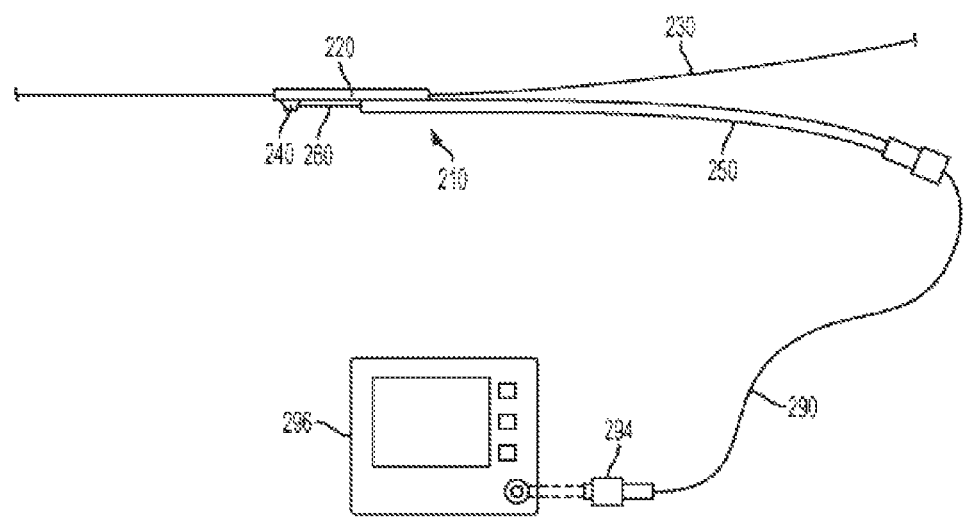
FIG. 3 is a perspective view of a sensor delivery device having a furcation tube according to embodiments of the invention.

FIG. 3 shows a device 210 according to an embodiment of the invention in which a proximal end of proximal portion 250 interconnects with a fiber optic furcation tube 290 (e.g., in embodiments of the invention employing a fiber optic sensor). A fiber optic furcation tube 290 provides an extension of the fiber optic communication channel 260 (from the sensor 240 through the proximal portion 250), to an optional connector 294, such as an "SC" fiber optic connector. Furcation tube 290 may, for example, be provided with SC connector 294 to allow the device 210 to send a signal from sensor 240 or an additional sensor, for example, to other devices, monitors, fluid injection devices, displays, or control units, etc.

The length of furcation tube 290 may be chosen to extend from the device 210 in the sterile field (e.g., where the patient is) to a location outside of the patient, such as a medical fluid injector, or to a standalone display device, or to some other processing or computing equipment 296 positioned some distance from the patient. The SC connector 294 is adapted to interconnect with an injector (or other signal processing unit) appropriately configured. If signal processing is done within the injector or other signal processing unit, then the display could be utilized to display pressure waveforms and/or to calculate and display FFR values which have been adjusted or corrected as described herein.

Figure 5:
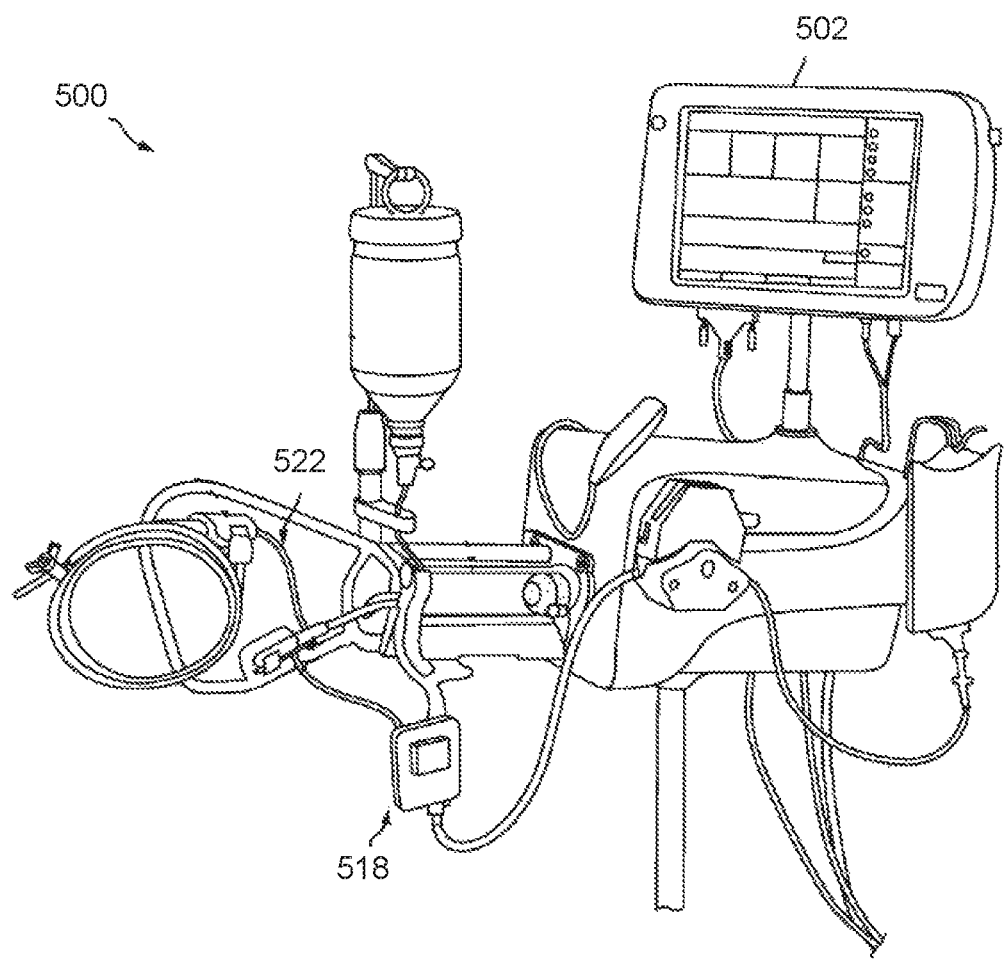
FIG. 5 is a perspective view of a fluid injection system that may be used to interact with a sensor delivery device according to embodiments of the invention.

It may be desirable, as mentioned above with respect to FIG. 3, to have the sensor delivery device 210 interact with other devices and/or display equipment. For example, a furcation tube 290 and a connector 294 may be used to send the signal (e.g., the measured physiological parameter signal or data) from sensor 240 to processing device 296 which can apply the correction factor to the measured pressure data or to the calculated FFR to obtain a corrected FFR or can apply the correction equation to the calculated FFR. Other sensor data may likewise be sent to the processing device 296. Processing device 296 could be, for example, a standalone display monitor to show signal waveforms and/or numerical values of the pressure signal from sensor 240 and/or other sensor data. Processing device 296 could include data recording capabilities such as a memory component in some embodiments or a memory component may be accessible to the processing device. In certain preferred embodiments of the invention, processing device 296 could comprise a medical fluid injection system, such as a powered fluid injector used to inject contrast media and/or saline during certain imaging procedures (e.g., angiography, computed tomography, Mill, ultrasound, etc.). FIG. 5 illustrates an exemplary powered injection system 500 which may be used with a sensor delivery device 210 according to various embodiments of the invention.

As noted above, the system 500 of FIG. 5 may be adapted to be coupled to a pressure sensing device such as a pressure sensor delivery device 210 according to certain embodiments of the invention. System 500 may, for example, be adapted to receive the pressure signal generated by the pressure sensor such as sensor 240 of device 210 and to perform calculations based on the pressure signal and/or other sensor data signals. In embodiments where the pressure signal from the pressure sensing device is a pressure signal measured downstream of a stenotic lesion (e.g., $P_d$), system 500 may calculate a corrected FFR, for example, since $P_p$ may already be provided by pressure transducer 518 of system 500. A visual or graphical display of the corrected FFR value could be presented to an operator via control panel 502, for example. In addition, time averaging or other signal processing could be employed by system 500 to produce mathematical variants of the corrected FFR calculation (e.g., mean, max, min, etc.). Alternately, a time-varying display or plot of the corrected FFR value could be displayed as a waveform (e.g., as a function of time).

Embodiments of the invention employ a correction factor, CF, or a correction equation, to correct the $P_d$ or FFR for the change in $P_d$ caused by the presence of the sensor delivery device 10 crossing to the stenosis. The change in pressure across a stenosis in a vessel can be calculated by using the following equation:

$$\Delta P = \frac{8\pi\mu L}{A_s}\frac{1}{A_s}Q + \frac{\rho k}{2}\left(\frac{1}{A_s}-\frac{1}{A_n}\right)^2 Q^2 \qquad \text{Eq. 1}$$

where $\Delta P$ is the pressure loss across the stenosis, $\mu$ is absolute blood viscosity, L is stenosis length, $A_n$ is the cross-sectional area of the normal artery, $A_s$ is the cross sectional area of the stenotic segment, V is the flow velocity, p is blood density, k=a constant related to entrance and exit effects, and Q is volume flow. The presence of the sensor delivery device 10 within the vessel at the stenotic lesion changes the cross sectional area through which the blood flows and therefore changes the $\Delta P$.

From an analysis based on Equation 1, a correction factor CF can be calculated to correct the FFR measured using a pressure sensing device such as sensor delivery device 10 for the effect of the additional area of the device crossing the lesion on the pressure measurements. This correction factor will depend upon the size (maximum outer diameter or cross-sectional area) of the device at the location of the lesion, with a larger device having a greater impact upon the measured pressure than a smaller device. However, because commercially available pressure sensing devices such as sensor delivery devices 10 are of a known size, the correction factor can be determined for each pressure sensing device and can be applied to measurements taken by that device. In some embodiments, additional variables, such as lesion size, vessel size, and blood flow rate (Q) may be used, separately or together, to adjust the correction factor CF for different circumstances.

The pressure drop across a stenosis, $\Delta P$, is defined as $P_p-P_d$. However, the presence of the sensor delivery device 10 across the stenosis causes a greater obstruction to blood flow such that the measured $P_d$ is less than the actual $P_d$ (without the presence of the sensor), and therefore the measured $\Delta P$ is less greater the actual $\Delta P$. Furthermore, because the sensor delivery device has a greater cross sectional area than a guidewire sensor (such as the 0.014 inch outer diameter guidewire sensors upon which the clinical cutoff points for FFR are typically based), the $\Delta P$ measured by such pressure sensing devices, such as the sensor delivery device 10, is also greater than the $\Delta P$ that would be measured by a 0.014 inch outer diameter guidewire sensor under the same conditions. A greater $\Delta P$ correlates to a lower FFR, which can lead to inaccurate treatment decisions if the FFR is not corrected to adjust for the error caused by the presence of the pressure sensing device, such as sensor delivery device 10, within the stenosis.

Embodiments of the invention employ a correction factor to reduce or eliminate the error due to the presence of the pressure sensing device, such as sensor delivery device 10, across a lesion as compared to a 0.014 inch outer diameter guidewire sensor, or alternatively as compared to a pressure sensing device of any other size or to a vessel with no sensor present. A correction factor (CF), which varies depending upon the cross sectional area of the sensor delivery device, can be used to calculate a corrected $\Delta P$ ($\Delta P_{corr}$) such that $\Delta P_{corr}=CF\cdot\Delta P$, where $\Delta P$ is the measured $\Delta P$ using a sensor delivery device 10. This relationship may also be written as $\Delta P_{corr}=CF(P_p-P_d)$. It can therefore also be understood that $\Delta P_{corr}=P_p-P_{dcorr}$, where $P_{dcorr}$ is the corrected $P_d$, and therefore $P_{dcorr}=P_p-\Delta P_{corr}$.

The corrected $\Delta P$, $\Delta P_{corr}$, can be used to calculate a corrected FFR, $FFR_{corr}$. Because $FFR=P_d/P_p$, then $FFR_{corr}=P_{dcorr}/P_p$. Furthermore, as shown above, $P_{dcorr}=P_p-\Delta P_{corr}$. Therefore, $FFR_{corr}=(P_p-\Delta P_{corr})/P_p$, which may be written alternatively as $FFR_{corr}=(P_p-\Delta P_{corr})/P_p$ or $FFR_{corr}=(P_p-CF\Delta P)/P_p$ or $FFR_{corr}=[P_p-CF(P_p-P_d)]/P_p$. In this way, the correction factor can be applied to the measured pressure values to calculate a corrected FFR. Such calculations can be performed by a processing device 296 which can apply the correction factor CF to the pressure to calculate the $FFR_{corr}$. The $FFR_{corr}$ may be the corrected value to approximate the FFR as measured by a traditional 0.014 inch outer diameter pressure sensing guidewire, by any other pressure sensing device, or the true FFR as would be the value with no measuring device present in the vessel.

In alternative embodiments, the correction factor CF may be calculated to be directly applied to the FFR (rather than to $\Delta P$ or $P_d$ as described above). In such cases, the CF may be calculated using Eq. 1 in the same way as described above. However, the measured $P_a$ and $P_d$ may be used to calculate the FFR, and the correction factor may be applied to the calculated FFR, such that $FFR_{corr}=FFR\cdot CF$.

In still other alternative embodiments, the calculated FFR value may be corrected using an equation, rather than a correction factor. The equation may be used to convert the calculated FFR, which may be calculated using the measured pressure values, to a corrected FFR. A different equation may be determined for each size (maximum outer diameter or cross-sectional area) of pressure sensing device and for correction or approximation to each alternative sensor system (including a traditional pressure sensing guidewire and a native vessel with no system). In some embodiments, the equations may apply to all blood flow rates, vessel sizes and lesion sizes. The processing device 296 may select the correction equation to be used based on the size or identity of the sensor delivery device. Alternatively, different equations may be created for not only each size of sensor delivery device 10, but also for other variables including one or more (or all) of blood flow, vessel size and lesion size. In such embodiments, sensors on the sensor delivery device 10 may measure these variables or these variables may be input by a user, based on separate measurements or estimates for example, and these measurements may be used, such as by processing device 296, to select the appropriate equation. The processing device 296 may use the pressure sensor data to calculate the FFR and may then apply the appropriate selected equation, based on sensed data and/or user input, to calculate the $FFR_{corr}$. For example, the user may input data such as the type of FFR correction required (such as to a 0.014 inch pressure sensing guidewire, to a native vessel, or to a different sized sensor) or the type/identity or size of sensor delivery device 10 being used in the procedure. In some embodiments, the only type of FFR correction which may be made is to approximate the FFR that would be measured by a 0.014 inch pressure sensing guidewire. The sensor delivery device 10 may include a component such as an identification component on a secondary communications channel or a radiofrequency identification (RFID) tag, for example, to directly provide data to the processing device such as the size of the device 10 or identification of its type, which may be used by the processing device 296 to determine its size, such as by using a look up table which may be stored in the memory.

The equation for a particular pressure sensing device, such as sensor delivery device 10, may be determined mathematically by comparing the calculated FFR found using the pressures measured by the device to the FFR that would be found under the alternative situation (such as the FFR as measured using a 0.014 inch pressure sensing guidewire, a different pressure sensing device, or a native vessel). These FFR values may be theoretical and may be calculated using equation 1. Alternatively, the FFR values may be measured using an actual sensor delivery device, guidewire sensor, or other pressure sensing device, in a simulated vessel with a simulated lesion, such as those disclosed in Hemodynamic diagnostics of epicardial coronary stenosis: in-vitro experimental and computational study, R K Banerjee et al., Biomedical Engineering Online 2008. FFR measurements may be obtained or calculated under a variety of conditions, such as various vessel sizes, flow rates, or lesion sizes. In some embodiments, the FFR values for all variable situations may be used together to calculate the correction equation for a pressure sensing device of a particular size. In such embodiments, the equation may be used under any of the variable situations (with any flow rate, lesion size or vessel size) for a particular size of pressure sensing device. In other embodiments, the FFR values may be separated according to one or more of the variables instead of, or in addition to, the size of the device for determination of the correction equation. In such cases, separate equations may be made for each alternative variable, or for various combinations of variables to be applied depending upon the environment in which the device is used and/or the size of device 10.

For example, in some embodiments, a single FFR correction equation may be used for a particular size of pressure sensing device under all circumstances. In other embodiments, various correction equations may apply to each particular size of pressure sensing device. For example, each sized device may have multiple correction equations, such as separate equations for various vessel sizes, separate correction equations for various lesion sizes, and/or separate correction equations for various blood flow rates, or any combination of two or more of these, or all three. Thus, for each size of pressure sensing device, there may be multiple FFR correction equations, and the one to be applied may be selected by the processing device 296, depending upon data received from the device and/or the user regarding the environment, such as the lesion size, the vessel size, and/or the blood flow rate, as well as data regarding the size of the pressure sensing device. In some embodiments, the selection of the correction equation may also depend on the type of correction desired, such as a correction to approximate an FFR as obtained by a 0.014 inch pressure sensing guidewire or other pressure sensing device or native vessel, which may be received from the user, or the type of correction may be selected automatically.

Figure 4A:
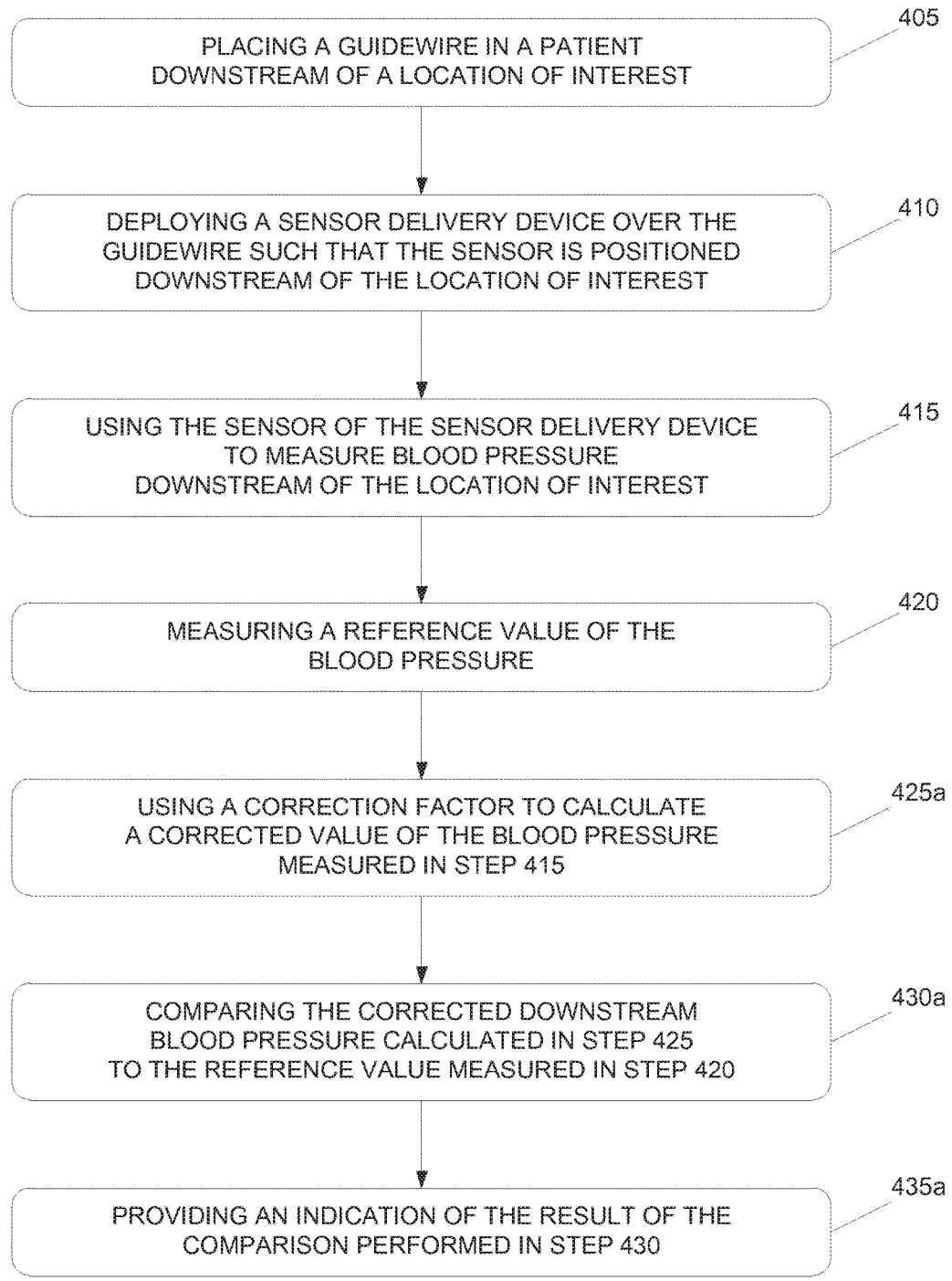
FIGS. 4a and 4b are flow diagrams showing methods of using a sensor delivery device according to embodiments of the invention.
Figure 4B:
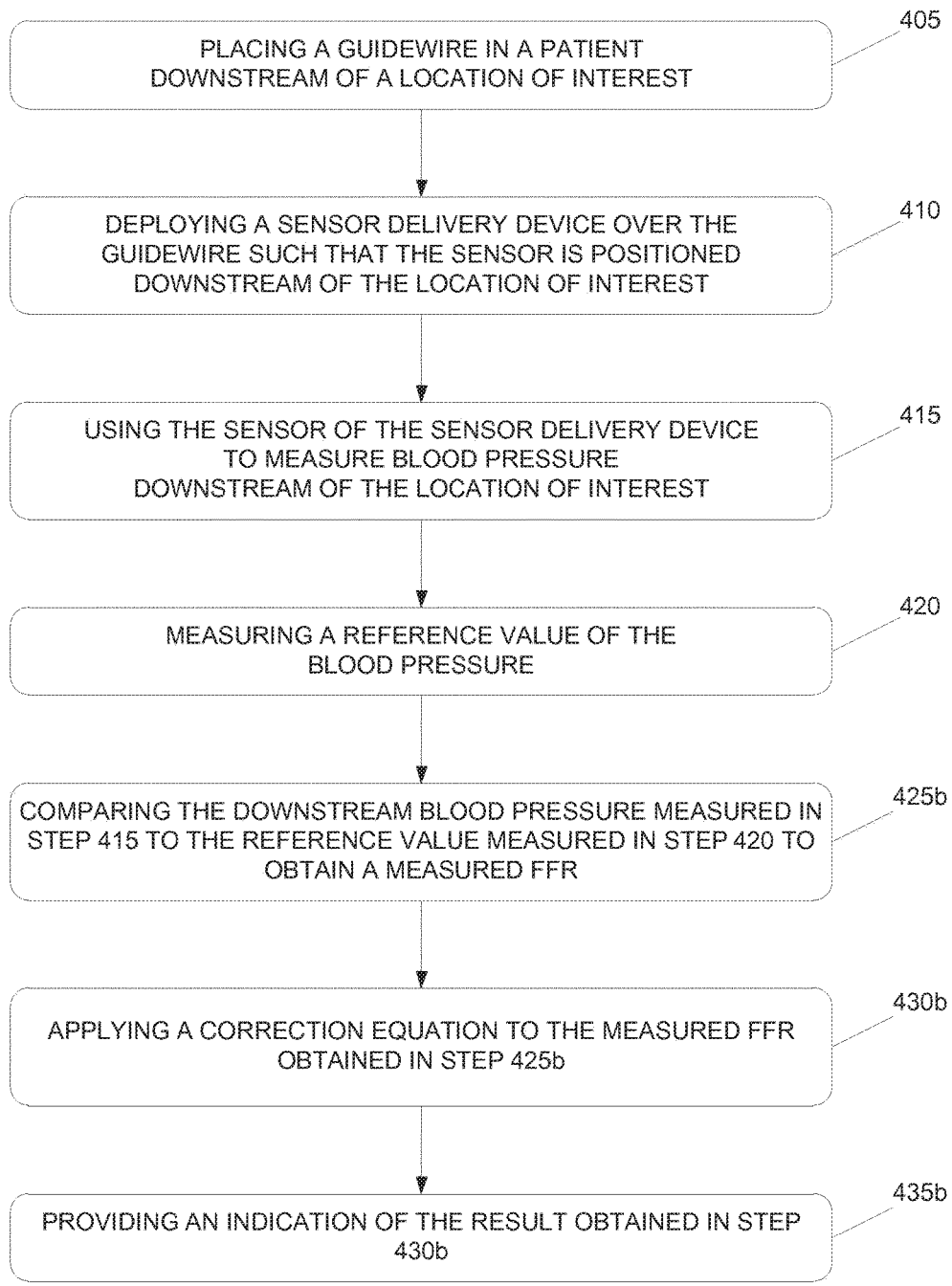

FIGS. 4a and 4b are flow diagrams showing methods of using a pressure sensing device, such as a sensor delivery device 10, according to certain embodiments. In a preferred embodiment of the invention, for example, the method may be used to assess the severity of a stenotic lesion in a patient's vasculature. Step 405 comprises placing a guidewire in a patient to a location of interest. In some embodiments, this may be a diagnostic guidewire, and a guiding catheter may also be inserted into the patient in conjunction with the guidewire. Step 410 comprises deploying a sensor delivery device 10 over the guidewire 30 such that the sensor 40 is positioned downstream of the location of interest (e.g., downstream of a stenotic lesion). The sensor delivery device 10 includes a sensor 40 mounted to a distal sleeve 20 that slides over the guidewire 30, and a proximal portion 50 that is used to advance the distal sleeve 20 over the guidewire 30 without having to move the guidewire 30. In alternative embodiments, a different pressure sensing device such as a pressure sensing guidewire or other over the wire device may be used instead. Step 415 comprises using the sensor 40 of the sensor delivery device 10 to measure blood pressure downstream of the location of interest. In some embodiments, the sensor measures blood pressure downstream of a stenotic lesion, $P_d$. Step 420 comprises measuring a reference value of the blood pressure. In some embodiments, this step comprises measuring blood pressure upstream of a stenotic lesion, $P_p$. This could be done, for example, with a separate blood pressure monitoring apparatus, according to some embodiments, by repositioning the sensor delivery device 10 to a location upstream of the stenotic lesion and making a second pressure measurement with the sensor 40 of the device or by measuring blood pressure using a second sensor 242 without repositioning the sensor delivery device 10 or by having a separate device. In FIG. 4a, step 425a comprises using a correction factor to calculate a corrected value of the downstream blood pressure measured in step 415. Step 430a comprises comparing the corrected blood pressure measured downstream of the location of interest and corrected in step 425 to the reference value measured in step 420. In some embodiments, this may comprise calculating a ratio of the two measured values. In one preferred embodiment of the invention, step 430 comprises calculating a corrected FFR (FFR$_{corr}$) as the ratio of the corrected downstream pressure to the upstream blood pressures, P$_{dcorr}$/P$_p$. Alternatively, in FIG. 4b, step 425b comprises comparing the downstream blood pressure measured in step 415 to the reference value measured in step 420 to obtain a measured FFR. Step 430b comprises applying a correction equation to the measured FFR obtained in step 425b. Alternatively, an FFR correction factor could be applied to the measured FFR. Steps 435a and 435b are optional steps which comprise providing an indication of the result obtained in steps 430a and 430b. For example, steps 435a and 435b may comprise providing a visual indication of the FFR$_{corr}$ value, or providing provide other visual cues (e.g., providing a color-coded indication of the severity of a stenotic lesion, such as a red indicator for FFR$_{corr}$ values less than a cutoff value such as 0.75 or 0.80, and a green indicator for FFR$_{corr}$ values equal to or greater than the cutoff value, as possible examples).

The system, such as the processing device 296, or the operator, may select the appropriate correction factor or correction equation. For example, the operator may input information such as the type or identity of sensor delivery device 10, the size of the sensor delivery device 10 into the system, and/or one or more physiological parameters of the patient such as vessel size, lesion size or blood flow rate, or the sensor delivery device 10 could provide data to the system identifying the sensor, the size of the sensor delivery device 10, and/or one or more physiological patient parameters. The system may then refer to a look up table to determine the appropriate correction factor or correction equation to be used based on this data. The look up table may be a set of two or more correction factors or correction equations which may be stored in a memory component of the system, such as in the processing device 296 or accessible to the processing device 296. Alternatively the user may input the appropriate correction factor or correction equation for the sensor delivery device 10 into the system, or the sensor delivery device 10 or other pressure sensing device could provide the data identifying the appropriate correction factor or correction equation to the system. The processing device 296 may include software or other computer executable code with which it is configured to select the correction factor or correction equation and to calculate a corrected FFR using the measured pressure data and the selected correction factor or correction equation.

Figure 6A:
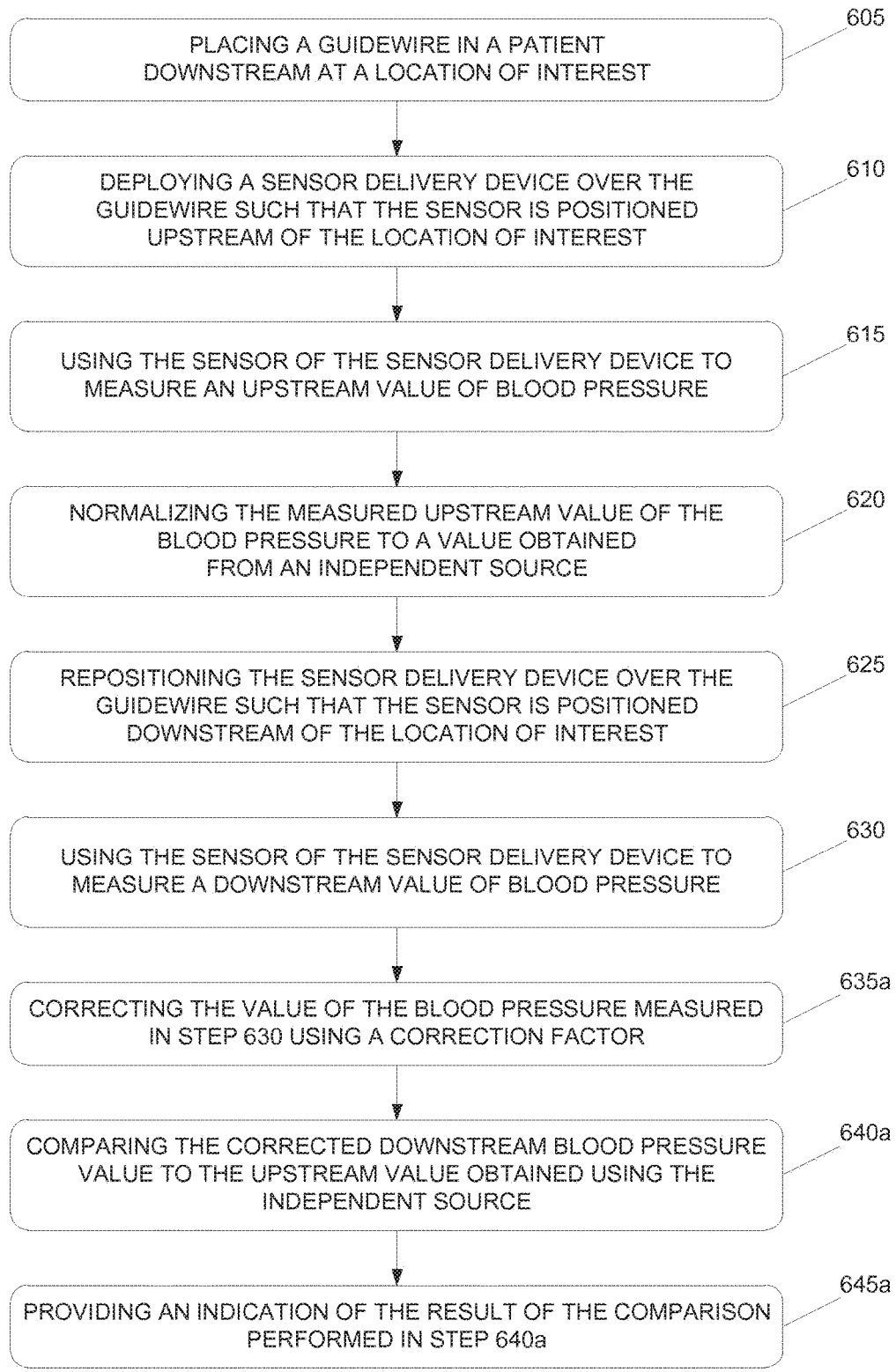
FIGS. 6a and 6b are flow diagrams of methods of using a sensor delivery device in conjunction with a fluid injection system according to embodiments of the invention.
Figure 6B:
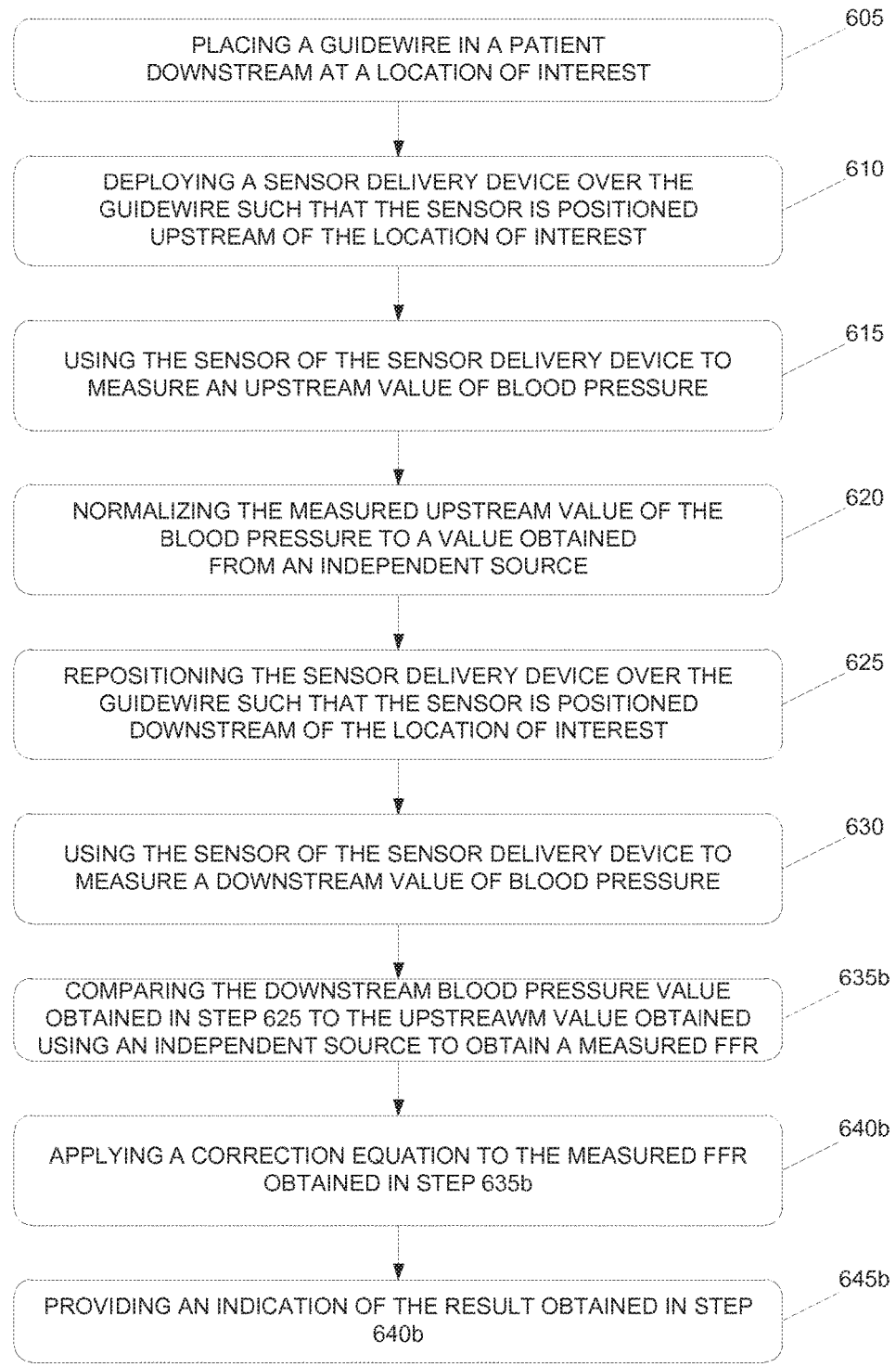

FIGS. 6a and 6b are flow diagrams of methods that may be performed according to some embodiments. The methods described herein may be performed in varying degrees of automation, for example, by having instructions stored in a computer-readable medium and/or performed by a computer or processor associated with a powered injection system (such as the ones described above with respect to FIG. 5, or other comparable fluid injection systems). The method of FIGS. 6a and 6b may, for example, be used to assess the severity of a fluid flow restriction in a patient according to some embodiments of the invention. The methods may be performed using various powered injection systems, such as the system 500 shown in FIG. 5. The ordering of the actions shown in FIGS. 6a and 6b is for exemplary purposes only. In one embodiment, a powered injection system may be capable of performing some of the steps of the methods shown in FIGS. 6a and 6b automatically, or alternately, after the operator has requested that the method be commenced through manual activation on the control panel (or secondary panel, if available).

Step 605 in FIGS. 6a and b comprises placing a guidewire 30 in a patient at a location of interest, such as a stenotic lesion, or across a heart valve, for example. In some embodiments, this may be a diagnostic guidewire, and a guiding catheter may also be inserted into the patient in conjunction with the guidewire. Step 610 comprises deploying a sensor delivery device 10 over the guidewire 30 such that the sensor 40 is positioned upstream of the location of interest (e.g., upstream of a stenotic lesion, or on the high pressure side of a valve). In some embodiments, the sensor delivery device 10 will have a sensor 40 mounted to a distal sleeve 20 that slides over the guidewire 30, and a proximal portion 50 that is used by an operator to advance the distal sleeve 20 over the guidewire 30 to the desired location without having to move the guidewire 30. Alternatively, other pressure sensing devices may be used. For example, the guidewire may be a pressure sensing guidewire, or a different over the wire pressure sensor may be used. Step 615 comprises using the sensor 40 of the sensor delivery device 10 to measure a value of blood pressure upstream of the location of interest. In some embodiments, the pressure measured by the sensor upstream of a stenotic lesion is the proximal pressure, P$_p$.

Step 620 in FIGS. 6a and 6b comprises "normalizing" the P$_p$ measurement made in step 615 to the P$_p$ measurement obtained from an independent source. "Normalizing" the P$_p$ measurement refers to the fact that an independent source (e.g., a fluid sensor for monitoring patient blood pressure during a procedure) will be used to obtain the P$_p$ value that will be used for later comparisons or calculations with the corrected P$_d$ value (e.g., the corrected downstream pressure) measured with the sensor 40 of the sensor delivery device 10 or other pressure sensing device and corrected by the correction factor. The normalizing step basically ensures that the P$_p$ value measured with the sensor 40 equals the P$_p$ value measured using the independent source so that no error is introduced (or that any error is minimized) when a subsequent downstream pressure measurement (e.g., P$_d$) is made. An adjustment, if needed, could be made to either P$_p$ value, although it may often be simpler to adjust the sensor-based P$_p$ value to match the independent source's P$_p$ value.

Step 625 comprises deploying the sensor delivery device 10 over the guidewire 30 or otherwise positioning the sensor of the pressure sensing device such that the sensor 40 is downstream of the location of interest (e.g., downstream of the stenotic lesion). Step 630 comprises using the sensor 40 of the sensor delivery device 10 or other pressure sensing device to measure a downstream value of blood pressure. In some embodiments, this step comprises measuring blood pressure downstream of the stenotic lesion, P$_d$. Step 635a in FIG. 6a comprises correcting the value of the blood pressure measured in step 630 using a correction factor. Step 640a comprises comparing the corrected blood pressure value downstream of the location of interest (e.g., P$_{dcorr}$, corrected downstream blood pressure) to a normalized value measured upstream of the location of interest or measured using the independent source (e.g., P$_p$). In some embodiments, the comparison made in step 640 may comprise calculating a ratio of the two values. In one preferred embodiment of the invention, step 640 comprises calculating the corrected FFR, FFR$_{corr}$, as the ratio of the corrected downstream blood pressure to the upstream blood pressure, P$_{dcorr}$/P$_p$. In FIG. 6b, step 635b comprises comparing the downstream blood pressure value obtained in step 625 to the upstream value obtained using an independent source to obtain a measured FFR. Step 640b comprises applying a correction equation to the measured FFR obtained in step 635b. Alternatively, an FFR correction factor may be applied to the measured FFR. Steps 645a and 645b are optional and comprise providing an indication of the result obtained in steps 640a and 640b. For example, steps 645a and 645b may comprise providing an indication of the $FFR_{corr}$ (e.g., numerical or graphical display or plot), and/or other cues may be provided to an operator. A color-coded indication of the severity of a stenotic lesion may be provided, for example, a red indicator for $FFR_{corr}$ values less than a cutoff value, and/or a green indicator for $FFR_{corr}$ values equal to or greater than a cutoff value. Other examples of indicators are possible, including non-visual indicators such as an audible indication, an alarm sound for example, could alert an operator of an $FFR_{corr}$ value that is less than a cutoff value, which may prompt the operator to make a therapy decision.

Figure 7A:
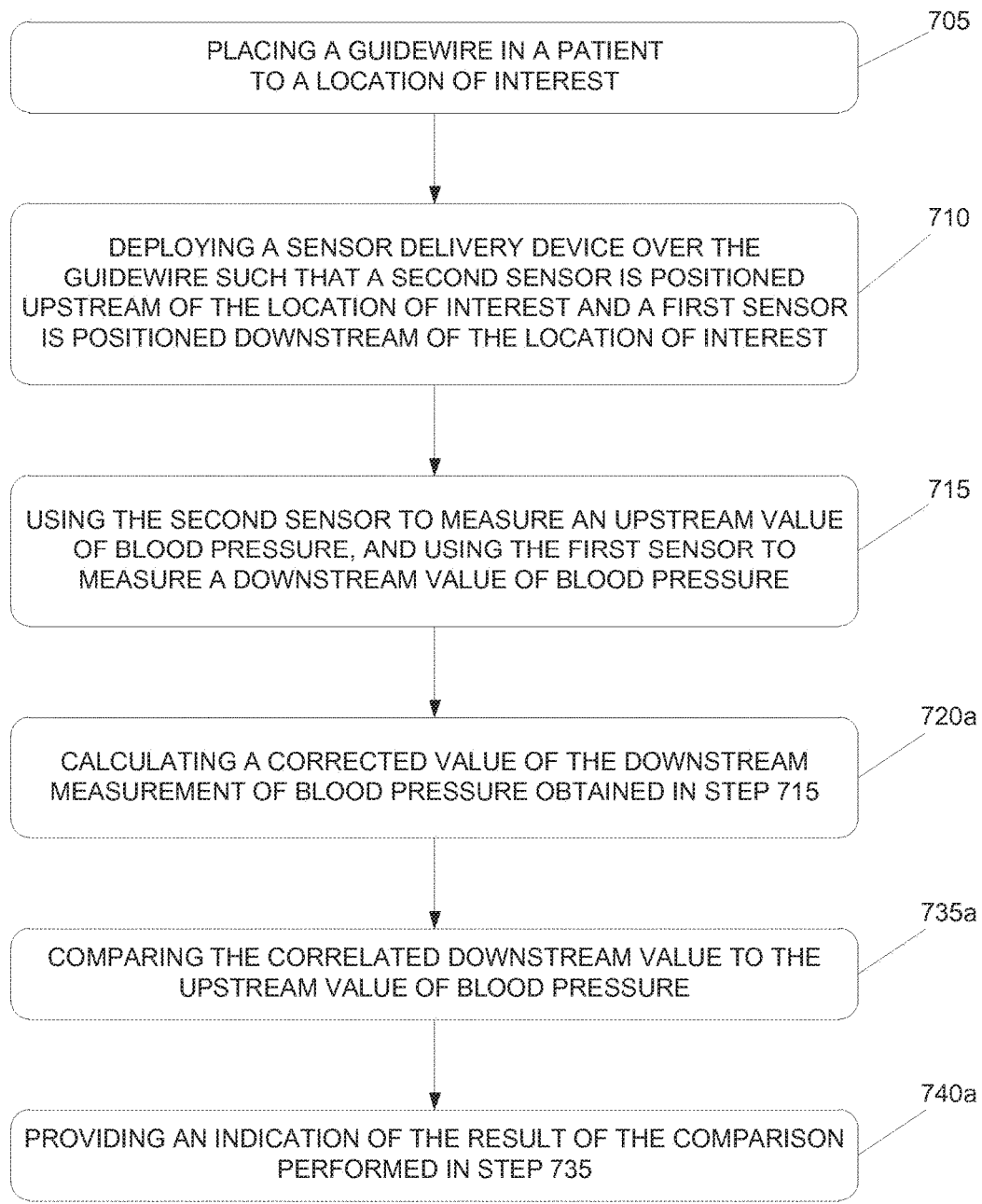
FIGS. 7a and 7b are flow diagrams of methods of using a sensor delivery device according to embodiments of the invention.
Figure 7B:
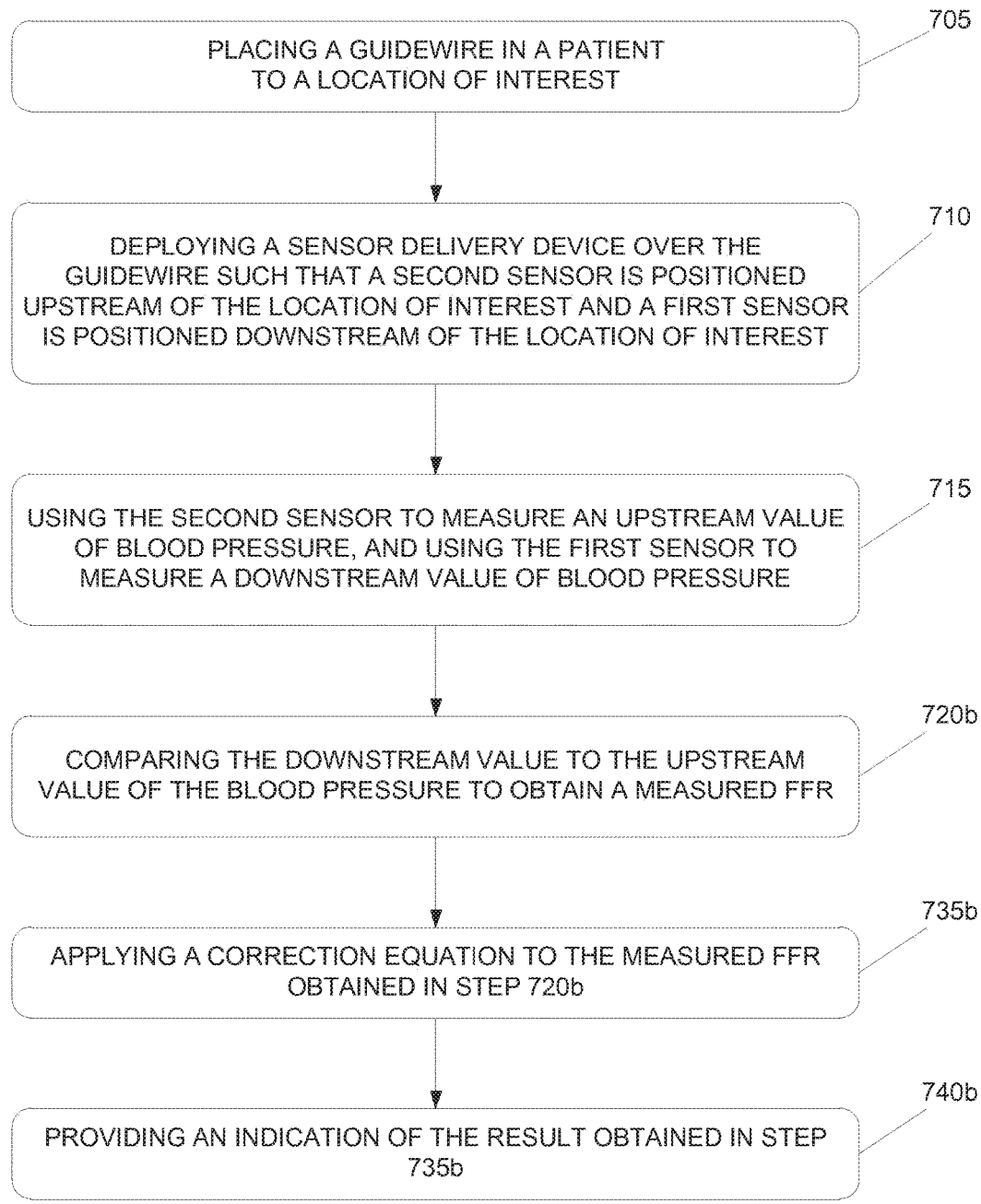
Figure 8:
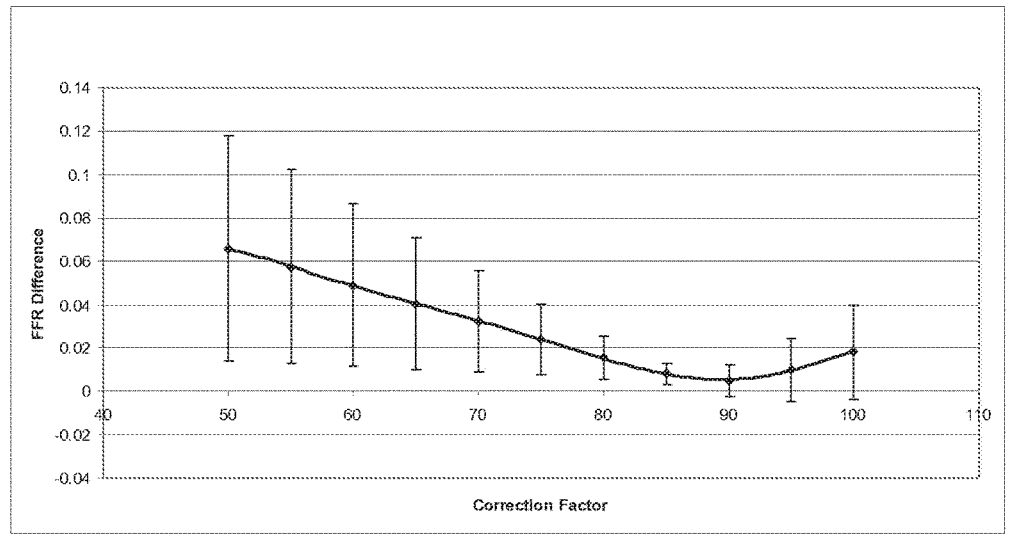
FIG. 8 is a graph of the difference between the theoretical corrected FFR and the theoretical FFR for a pressure sensing guidewire versus correction factor for a 0.018 inch device.
Figure 9:
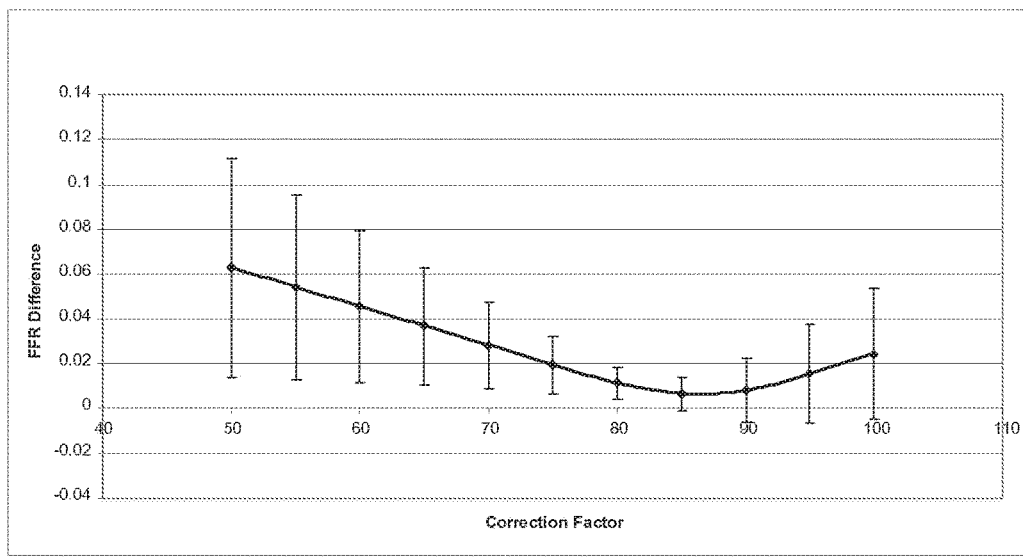
FIG. 9 is a graph of the difference between the theoretical corrected FFR and the theoretical FFR for a pressure sensing guidewire versus correction factor for a 0.019 inch device.
Figure 10:
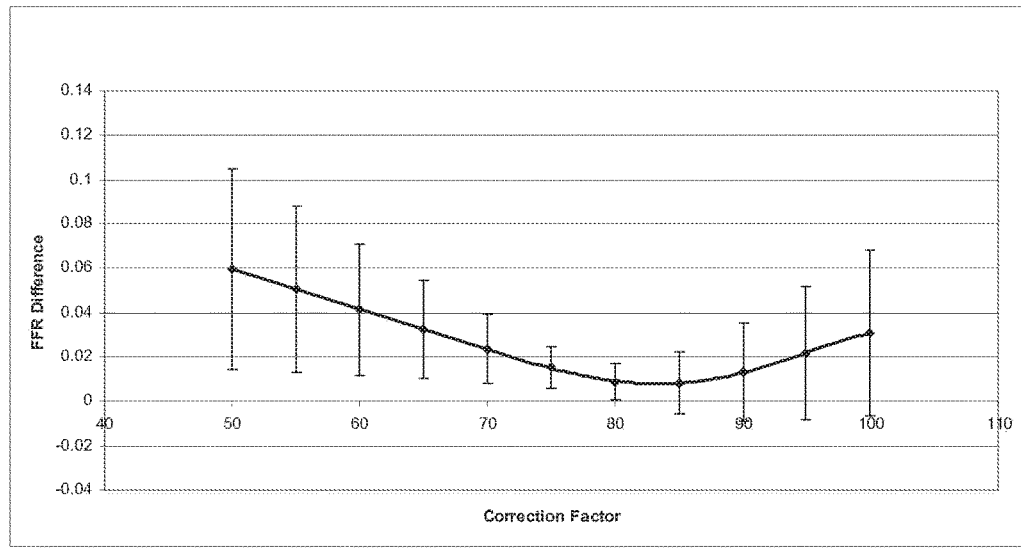
FIG. 10 is a graph of the difference between the theoretical corrected FFR and the theoretical FFR for a pressure sensing guidewire versus correction factor for a 0.020 inch device.
Figure 11:
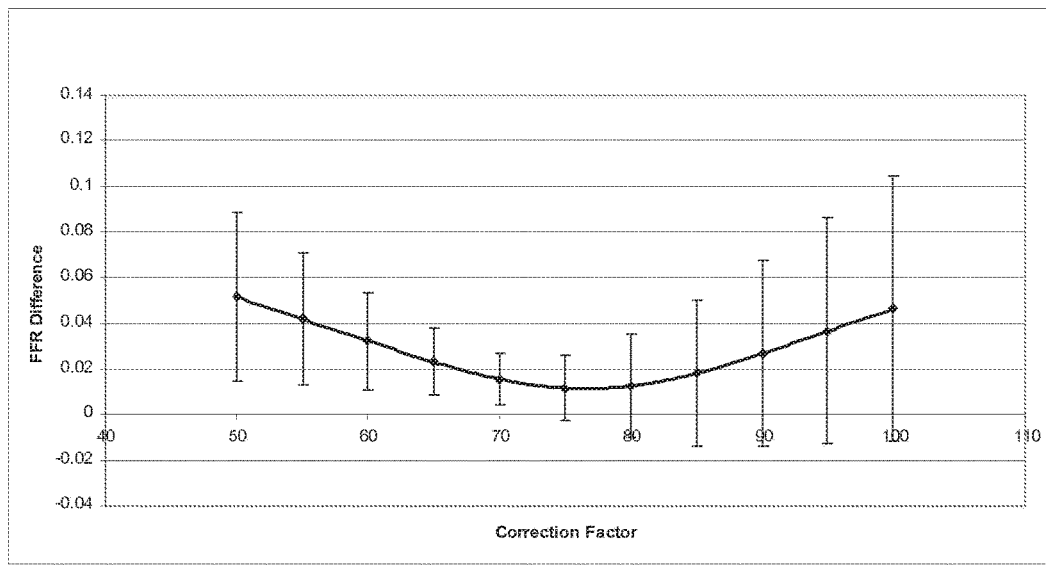
FIG. 11 is a graph of the difference between the theoretical corrected FFR and the theoretical FFR for a pressure sensing guidewire versus correction factor for a 0.022 inch device.
Figure 12:
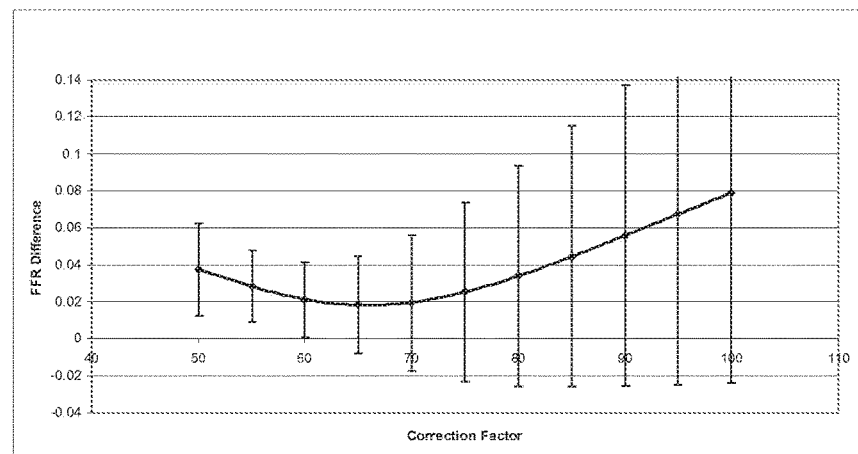
FIG. 12 is a graph of the difference between the theoretical corrected FFR and the theoretical FFR for a pressure sensing guidewire versus correction factor for a 0.025 inch device.
Figure 13:
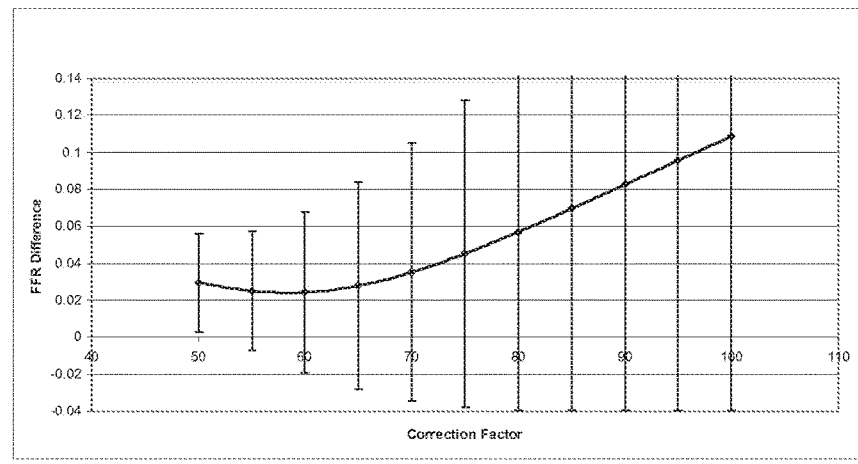
FIG. 13 is a graph of the difference between the theoretical corrected FFR and the theoretical FFR for a pressure sensing guidewire versus correction factor for a 0.027 inch device.

FIGS. 7a and 7b are flow diagrams of methods that may be performed according to various embodiments. The methods of FIGS. 7a and 7b may, for example, be used to assess the severity of a fluid flow restriction in a patient according to some embodiments of the invention. The methods of FIGS. 7a and 7b employ a sensor delivery device 210 having a first and second sensor 240, 242, such as the devices 210 shown in FIG. 2. Alternatively, other pressure sensing devices having first and second sensors may be used. This method may also be performed in conjunction with various powered injection systems, such as the system 500 shown in FIG. 5. The ordering of the actions shown in FIG. 7 is for exemplary purposes only.

Step 705 in FIG. 7 comprises placing a guidewire 230 in a patient to a location of interest, such as a stenotic lesion, or across a heart valve, for example. In some embodiments, the guidewire 230 may be a diagnostic guidewire, and a guiding catheter may also be inserted into the patient in conjunction with the guidewire. Step 710 comprises deploying a sensor delivery device 210 over the guidewire 230 such that a first sensor 240 of the sensor delivery device 210 is positioned downstream of the location of interest, and a second sensor 242 of the sensor delivery device 210 is positioned upstream of the location of interest. In some embodiments, an optional step may next be performed wherein a proximal sleeve 250 is moved by an operator relative to the rest of device 210 in order to vary the distance, V, between a first sensor and second sensor. Alternatively, other pressure sensing devices may be similarly positioned at the location of interest. In an embodiment such as that described above with respect to FIG. 2, it should be noted that more than two sensors could be mounted along device 210, and that the spacing between adjacent sensors could vary as well, according to some embodiments of the invention. Step 715 comprises using the second sensor 242 to measure an upstream value of the blood pressure, and using the first sensor 240 to measure a downstream value of the physiological parameter.

In FIG. 7a, the downstream value of the blood pressure is corrected in step 720a. Step 735a comprises comparing the corrected value downstream of the location of interest (e.g., $P_{dcorr}$, corrected downstream blood pressure) to the value measured upstream of the location of interest (e.g., $P_p$). In some embodiments, the comparison made in step 735a may comprise calculating a ratio of the two values. In one preferred embodiment of the invention, step 735 comprises calculating $FFR_{corr}$ as the ratio of corrected downstream to upstream blood pressures, $P_{dcorr}/P_p$. Alternatively, in FIG. 7b, step 720b comprises comparing the downstream value to the upstream value of the blood pressure to obtain a measured FFR. Step 735b comprises applying a correction equation to the measured FFR obtained in step 720b. Steps 740a and 740b, which may be optional steps, comprise providing an indication of the result obtained in steps 735a and 735b. For example, steps 740a and 740b may comprise providing an indication of the $FFR_{corr}$ value (e.g., numerical or graphical display or plot), and/or other cues may be provided to an operator. A color-coded indication of the severity of a stenotic lesion may be provided, for example, a red indicator for $FFR_{corr}$ values less than 0.75, and/or a green indicator for $FFR_{corr}$ values equal to or greater than 0.75 (or other cutoff values such as 0.80). Other examples of indicators are possible, including non-visual indicators such as an audible indication, an alarm sound for example, could alert an operator of an $FFR_{corr}$ value that is less than 0.75, which may prompt the operator to make a therapy decision.

The methods shown in FIGS. 4, 6, and 7 may include a step of selecting a correction factor or correction equation to be applied. The correction factor or correction equation may be selected based on the identity or size of the pressure sensing device as provided by user input or data from the device. It may further be selected based upon measured variables which may be measured by the device and/or provided by the operator including blood flow rate, lesion size and/or vessel size.

Any of these methods could be performed with an embodiment of device 210 having flow holes. Using such a device, the methods may optionally include a step wherein an operator retracts the guidewire 230 to allow fluid flow (e.g., blood flow) through flow holes into the guidewire lumen 222 of the distal sleeve 220. Performing this optional step prior to measuring downstream pressure, $P_d$, may reduce the amount of flow restriction caused by the device 210 itself, and may thereby reduce the measurement error.

While various embodiments of methods and systems of calculating a corrected FFR using sensor delivery devices are described herein, the invention is not limited to these sensor delivery devices. Rather, embodiments of the invention may be used to determine a corrected FFR for pressure measurements obtained using other pressure measuring devices as well.

In some embodiments, a method may include basing a therapy decision on the $FFR_{corr}$ value, e.g., if the $FFR_{corr}$ is less than 0.75 or less than 0.80, an interventional therapy is recommended and/or performed. In some embodiments, an interventional therapy device may be deployed by withdrawing sensor delivery device 210, and using the same guidewire 230 to deploy the interventional therapy device.

Example 1

An example of the calculation and application of a correction factor CF is described in this example. The formula of Eq. 1 was applied to theoretical vessels to calculate pressures proximal and distal to stenoses with varying degrees of occlusion, as those pressures would be under a range of physiological conditions, and as they would be under various measuring scenarios. Those measuring scenarios included true pressures (actual pressures, as would be present without the use of a measuring device, referred to as native vessels), with a theoretical pressure sensing guidewire present having an outer diameter of 0.014 inch in the vessel, and with various theoretical sensor delivery devices as described herein present in the vessel. These sensor delivery devices are identified as OD1 (0.018 inch outer diameter), OD2 (0.019 inch outer diameter), OD3 (0.020 inch outer diameter), OD4 (0.022 inch outer diameter), OD5

(0.025 inch outer diameter) and OD6 (0.027 inch outer diameter), and the calculations were performed for theoretical lesions having 20 to 80% occlusions (in 5% increments). The native vessel had inner diameters of 1.5 mm, 2 mm, 3 mm and 4 mm. Calculations were made for each condition and each degree of stenosis at blood flow velocities of 120, 150, 180, 210, 240, and 270 ml/min.

Using this data, a correction factor was empirically determined for each sensor delivery device as shown below in Table 1. The correction factor selected for each sensor delivery device to be used to calculate an $FFR_{corr}$ which would approximate the FFR as would be measured by the 0.014 inch guidewire sensor. In this example, the correction factor was derived using an iterative approach by applying a series of potential correction factors and analyzing the results. The correction factor in this example was selected as the value which was most accurate (closest to the FFR that would be obtained using a 0.014 inch pressure sensing guidewire) for FFR values close to the FFR cutoff value for therapeutic intervention when a 0.014 inch guidewire sensor is used, which in this case was taken to be 0.75. The correction factors obtained in this example could be applied to any measurement made with a sensor delivery device of a particular size, regardless of the blood flow velocity, vessel size or degree of stenosis since pressure measurements of that would occur under ranges of these variables were included in the calculations for each size of sensor delivery device. (In other embodiments, a different correction factor may be determined for difference blood flow velocities, vessel sizes, and/or degrees of stenosis/lesion sizes.)

TABLE 1

| Guidewire OD (in) | Correction Factors |
| --- | --- |
| Sensor OD 1 | 83 |
| Sensor OD 2 | 78 |
| Sensor OD 3 | 73 |
| Sensor OD 4 | 68 |
| Sensor OD 5 | 63 |
| Sensor OD 6 | 58 |

The correction factors of Table 1 were then applied to the theoretical calculated pressure measurements to calculate corrected pressure differences and corrected FFRs.

By applying the correction factor to the theoretical values, $FFR_{corr}$ was obtained which was very close to the calculated FFR for the 0.014 pressure sensing guidewire for each sensor delivery device. The difference between the theoretical corrected FFR for each sensor delivery device and the theoretical FFR of the 0.014 inch guidewire sensor was found to be quite low for all sensor sizes, degrees of stenosis, and blood flow rates, indicating that the correction factor properly corrected the FFR under each of these varying conditions. While the correction factor was less accurate at correcting the FFR as FFR moved further from the therapeutic cutoff point of 0.75, this greater degree of variation is not problematic because it does not affect the clinical decision regarding whether or not to treat. Rather, by calculating the correction factor to be most accurate around the clinical treatment cutoff value, such as to be most accurate at about 10% above and below the cutoff value, for example, the system is able to eliminate error caused by the presence of the sensor delivery device 10 which could otherwise lead to an inaccurate treatment decision. This data shows that the pressure sensing devices of various sizes which are of a different size than 0.014 inch outer diameter guidewire sensors may be used and the pressure measurements may be adjusted to calculate a corrected FFR that can be used for clinical decision making. In this way, clinicians can enjoy the advantages of various pressure sensing devices, such as sensor delivery devices which can be deployed over any guidewire selected or preferred by the clinician, and the data which is obtained can be used for clinical decision making in the same way as data obtained using traditional pressure sensing guidelines.

Example 2

Theoretical pressure data was again generated according to the method described in Example 1, but only for theoretical vessels having diameters of 2 mm, 3 mm and 4 mm. For all of the theoretical measurements for each size of device, a computer model calculated the FFR difference as the difference between the FFR as would be measured by a 0.014 inch outer diameter pressure sensing guidewire FFR and the FFR as would be measured by the sensor delivery device. The absolute value of the FFR difference for all theoretical measurements for each device were then averaged. The correction factor was then iterated and applied to the values, using Microsoft Excel Solver, until the correction factor producing the minimum average FFR difference was determined for each size of sensory delivery device. This correction factor represents the correction factor which produces the minimum error between the device and the 0.014 inch outer diameter pressure sensing guidewire and is therefore an optimum correction factor. FIGS. 8-13 show the difference between the corrected FFR and the FFR for a 0.014 inch pressure sensing guidewire for difference sized devices, and the results are summarized in Table 2, below. The data in FIGS. 8, 9, 10, 11, 12, and 13 are for devices having outer diameters of 0.018, 0.019, 0.020, 0.022, 0.025 and 0.027 inches respectively, and the nadir of each curve represents the optimized correction factor, listed below in table 2.

TABLE 2

| Outer Diameter (in) | Optimized Correction Factor | Average Corrected FFR difference |
| --- | --- | --- |
| 0.018 | 0.894 | 0.005 +/− 0.007 |
| 0.019 | 0.865 | 0.006 +/− 0.009 |
| 0.020 | 0.835 | 0.008 +/− 0.011 |
| 0.022 | 0.771 | 0.011 +/− 0.018 |
| 0.025 | 0.671 | 0.02 +/− 0.03 |
| 0.027 | 0.601 | 0.02 +/− 0.04 |

As can be seen in the Figures and from Table 2, the optimized correction factor was able to minimize the difference between the corrected FFR and the FFR as obtained using a 0.014 inch pressure sensing guidewire. The use of the correction factor therefore represents a good method of using pressure reading obtained using pressure sensing devices of various sizes to approximate the FFR value that would be obtained using a 0.014 inch pressure sensing guidewire.

Figure 14:
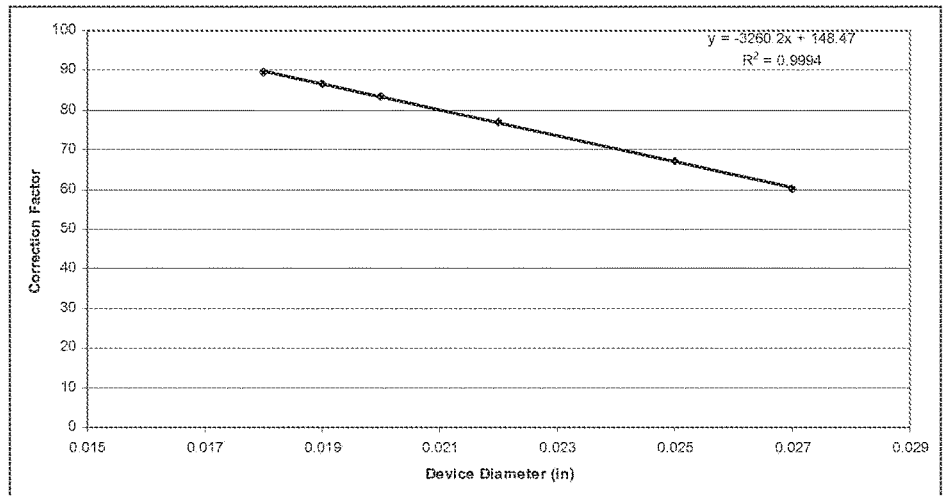
FIG. 14 is a graph correction factor versus device diameter.

FIG. 14 is a plot of the correction factors as indicated in Table 2 verses theoretical sensor delivery device diameter and reveals a linear relationship. This linear relationship allows for interpolation of a correction factor based on actual outer diameters (cross sectional areas) that may be different from those used to make the calculations, so that accurate correction factors can be determined for pressure sensing devices of any size.

Figure 15A:
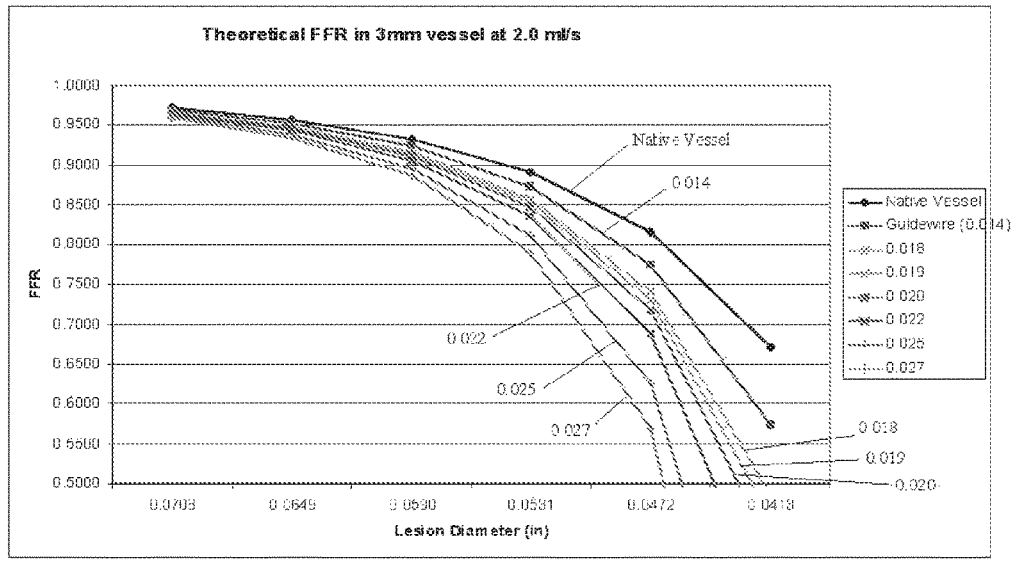
FIG. 15a is a graph of theoretical FFR values for various devices for a blood flow rate of 2.0 ml/s.
Figure 15B:
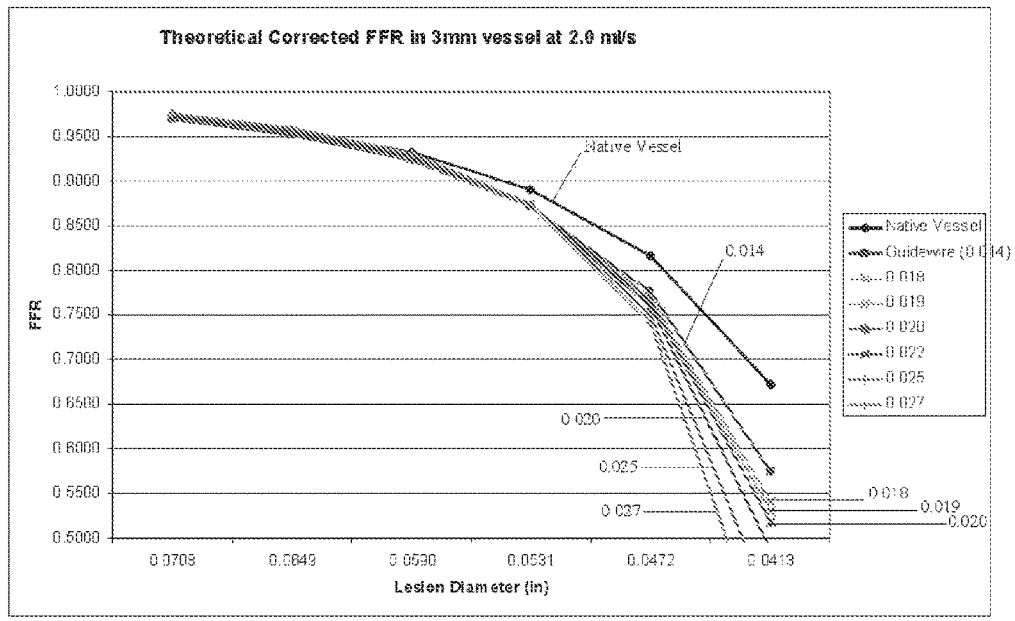
FIG. 15b is a graph of corrected theoretical FFR values for various devices for a blood flow rate of 2.0 ml/s.
Figure 15C:
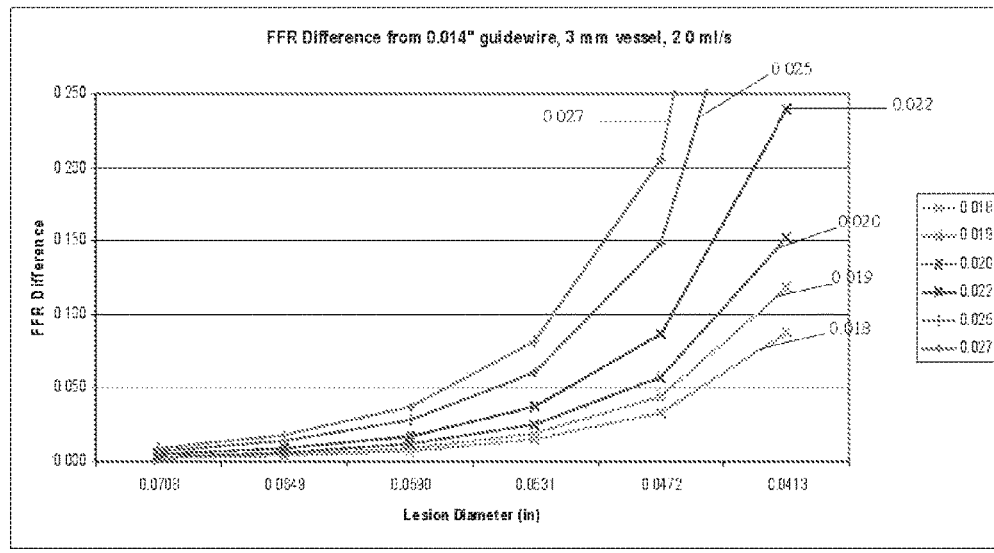
FIG. 15c is a graph of the difference between the theoretical FFR values and the FFR values for a 0.014 inch pressure sensing guidewire for various devices at a blood flow rate of 2.0 ml/s.
Figure 15D:
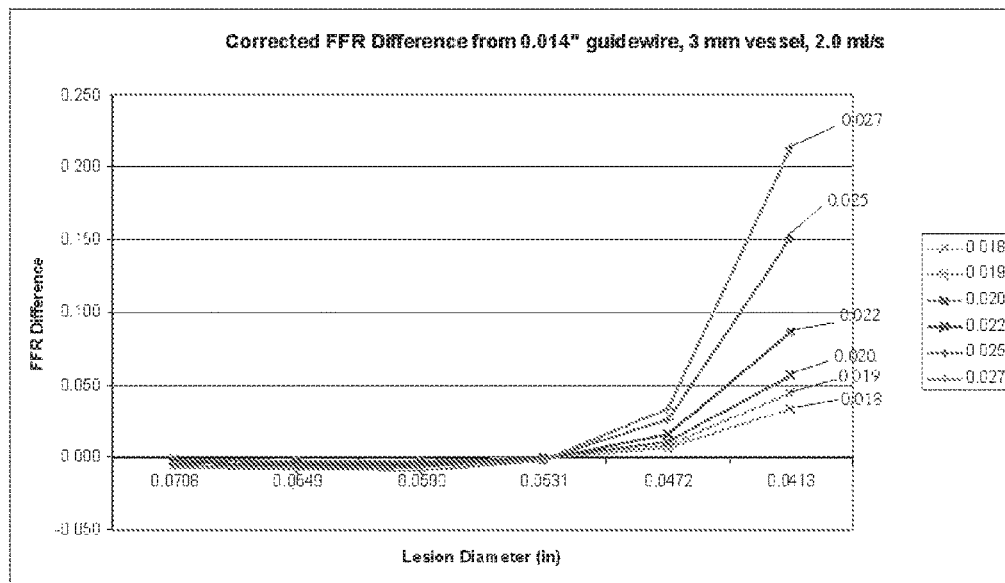
FIG. 15d is a graph of the difference between the theoretical corrected FFR values and the FFR value for a 0.014 inch pressure sensing guidewire for various devices at a blood flow rate of 2.0 ml/s.
Figure 16A:
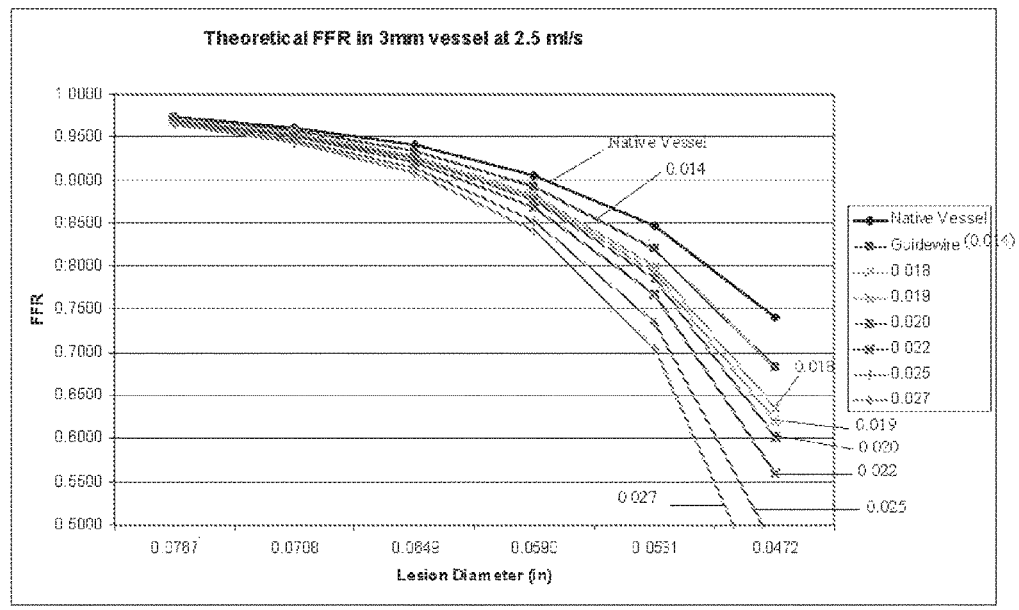
FIG. 16a is a graph of theoretical FFR values for various devices for a blood flow rate of 2.5 ml/s.
Figure 16B:
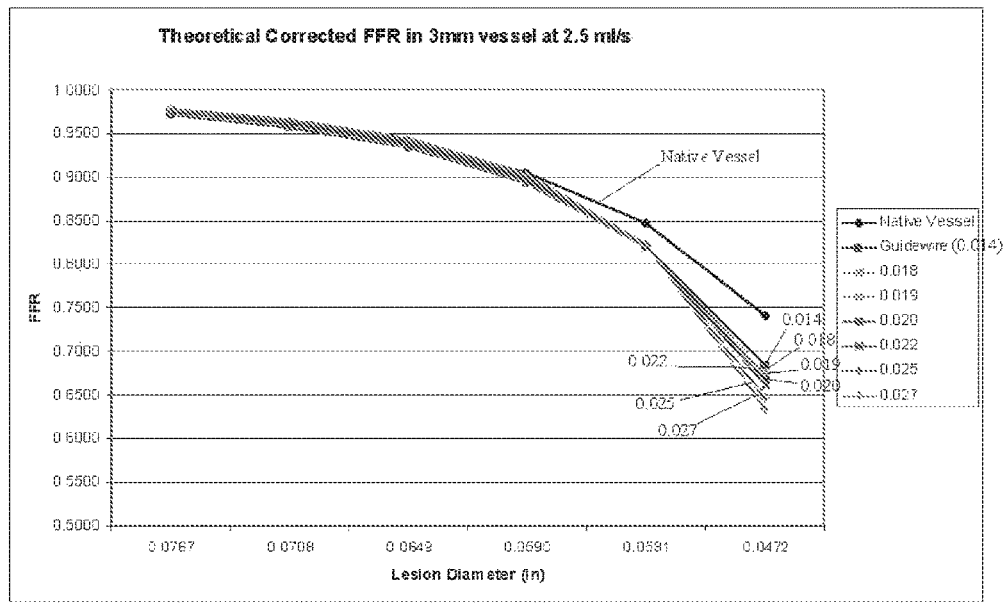
FIG. 16b is a graph of corrected theoretical FFR values for various devices for a blood flow rate of 2.5 ml/s.
Figure 16C:
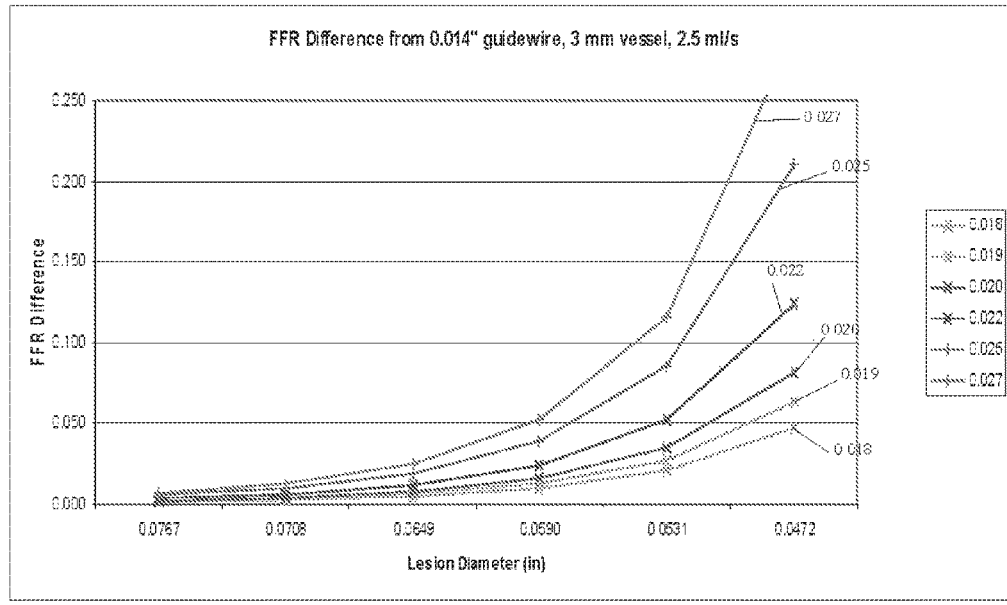
FIG. 16c is a graph of the difference between the theoretical FFR values and the FFR values for a 0.014 inch pressure sensing guidewire for various devices at a blood flow rate of 2.5 ml/s.
Figure 16D:
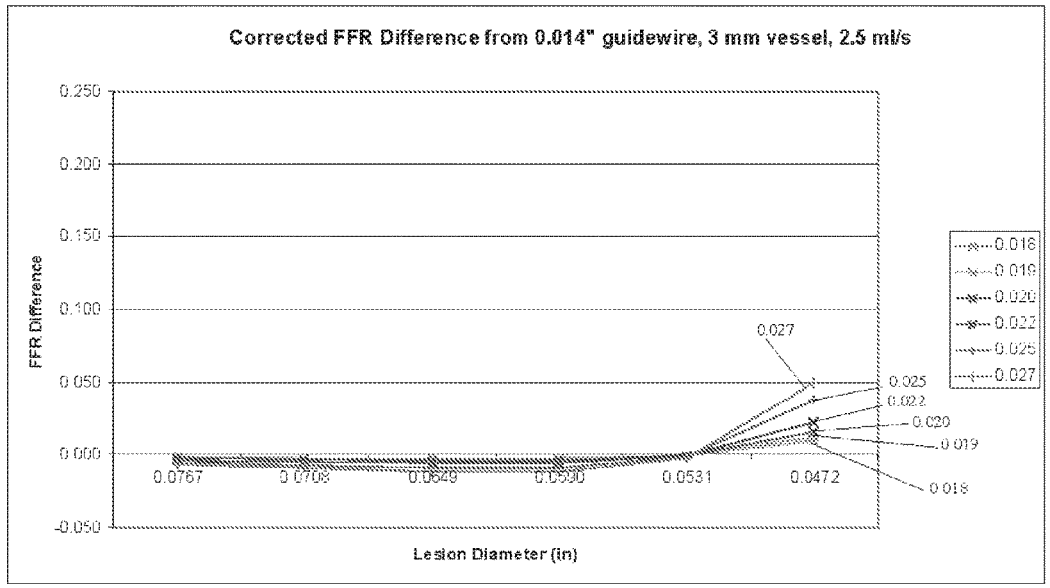
FIG. 16d is a graph of the difference between the theoretical corrected FFR values and the FFR value for a 0.014 inch pressure sensing guidewire for various devices at a blood flow rate of 2.0 ml/s.
Figure 17A:
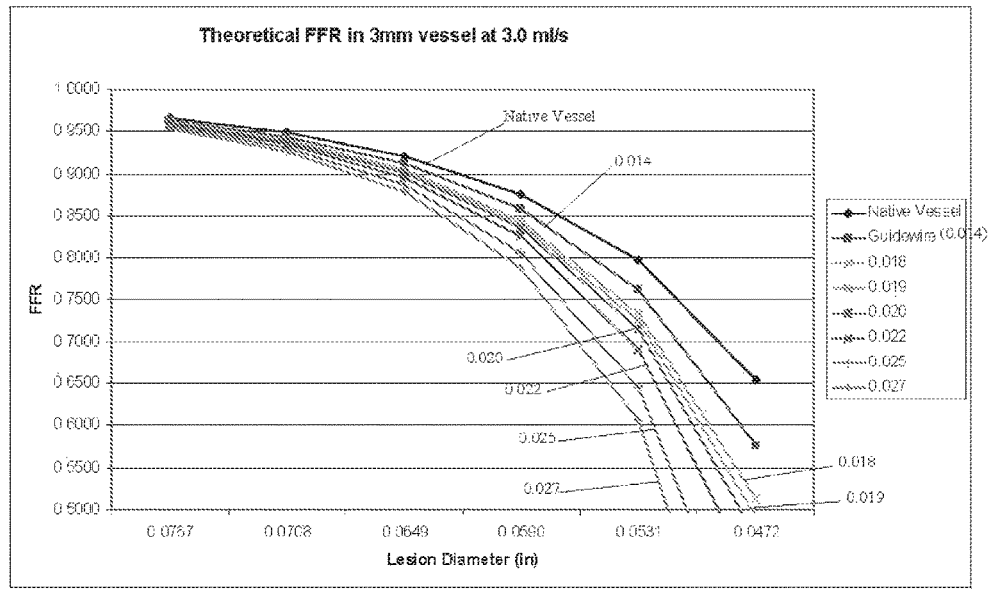
FIG. 17a is a graph of theoretical FFR values for various devices for a blood flow rate of 3.0 ml/s.
Figure 17B:
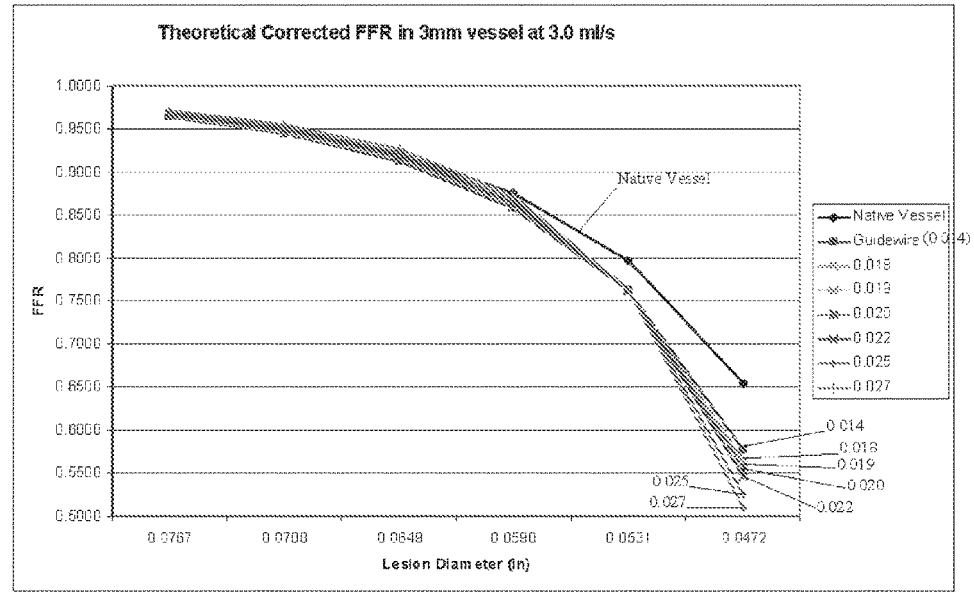
FIG. 17b is a graph of corrected theoretical FFR values for various devices for a blood flow rate of 3.0 ml/s.
Figure 17C:
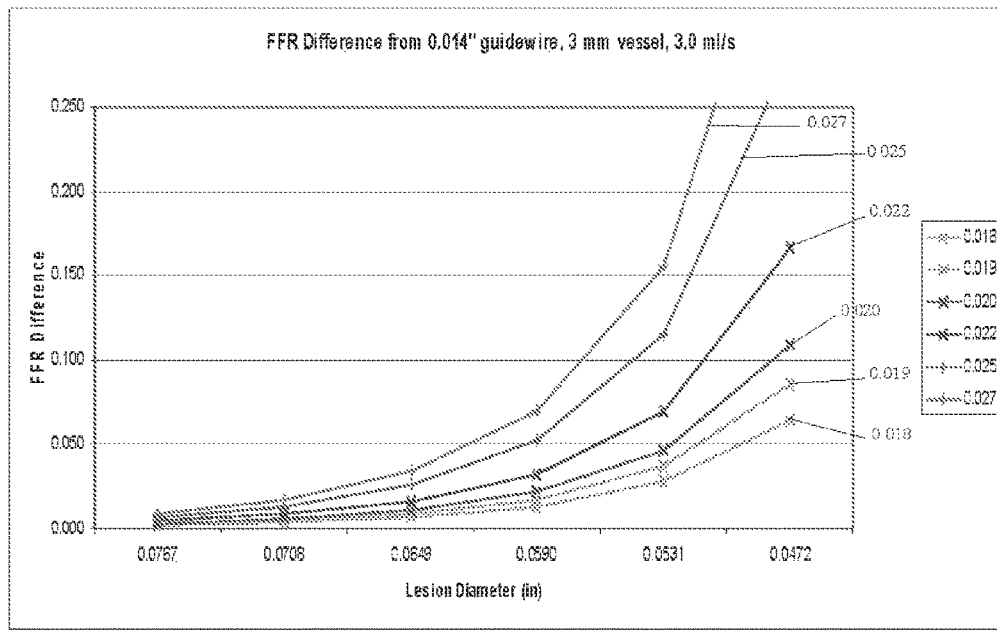
FIG. 17c is a graph of the difference between the theoretical FFR values and the FFR values for a 0.014 inch pressure sensing guidewire for various devices at a blood flow rate of 3.0 ml/s.
Figure 17D:
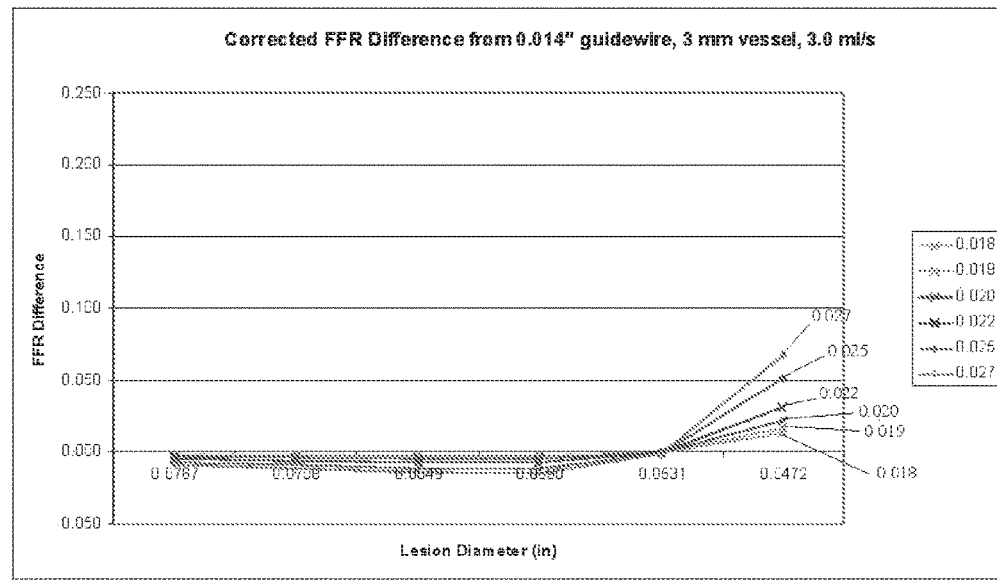
FIG. 17d is a graph of the difference between the theoretical corrected FFR values and the FFR value for a 0.014 inch pressure sensing guidewire for various devices at a blood flow rate of 3.0 ml/s.
Figure 18A:
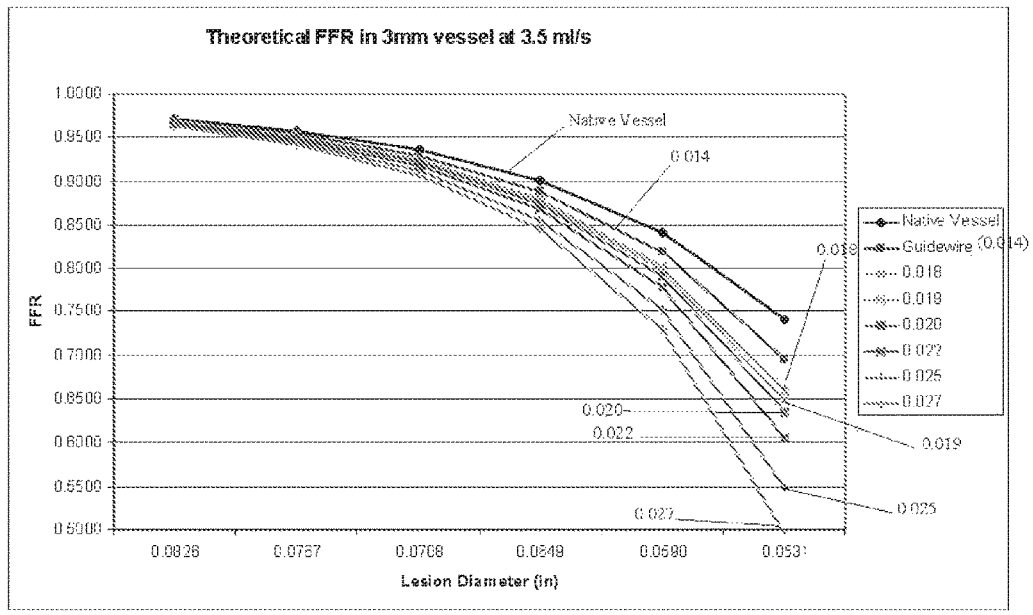
FIG. 18a is a graph of theoretical FFR values for various devices for a blood flow rate of 3.5 ml/s.
Figure 18B:
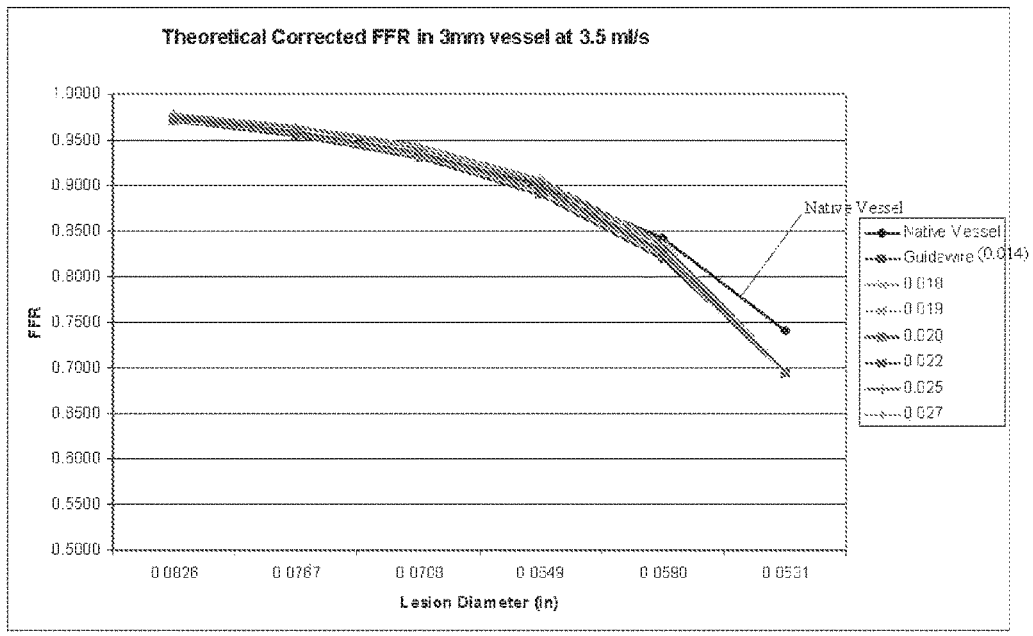
FIG. 18b is a graph of corrected theoretical FFR values for various devices for a blood flow rate of 3.5 ml/s.
Figure 18C:
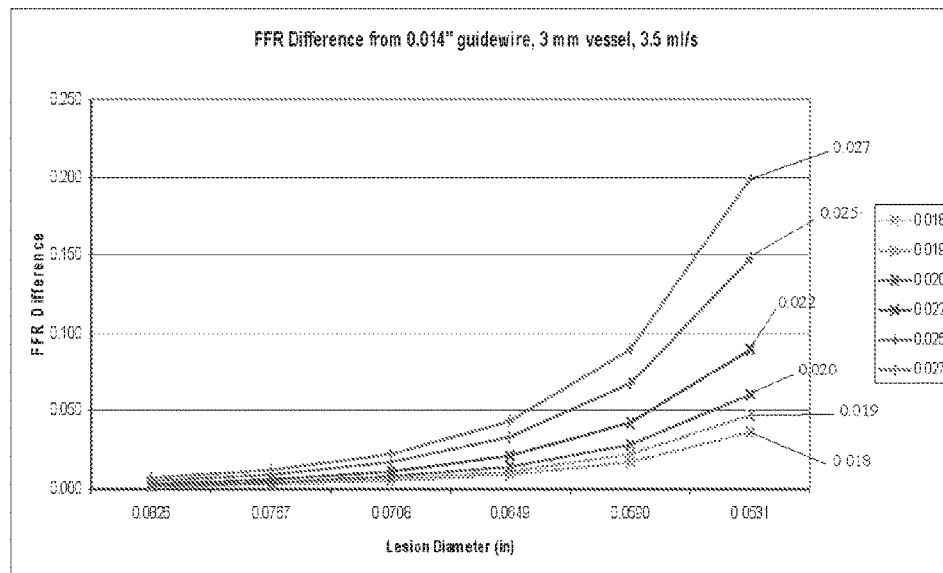
FIG. 18c is a graph of the difference between the theoretical FFR values and the FFR values for a 0.014 inch pressure sensing guidewire for various devices at a blood flow rate of 3.5 ml/s.
Figure 18D:
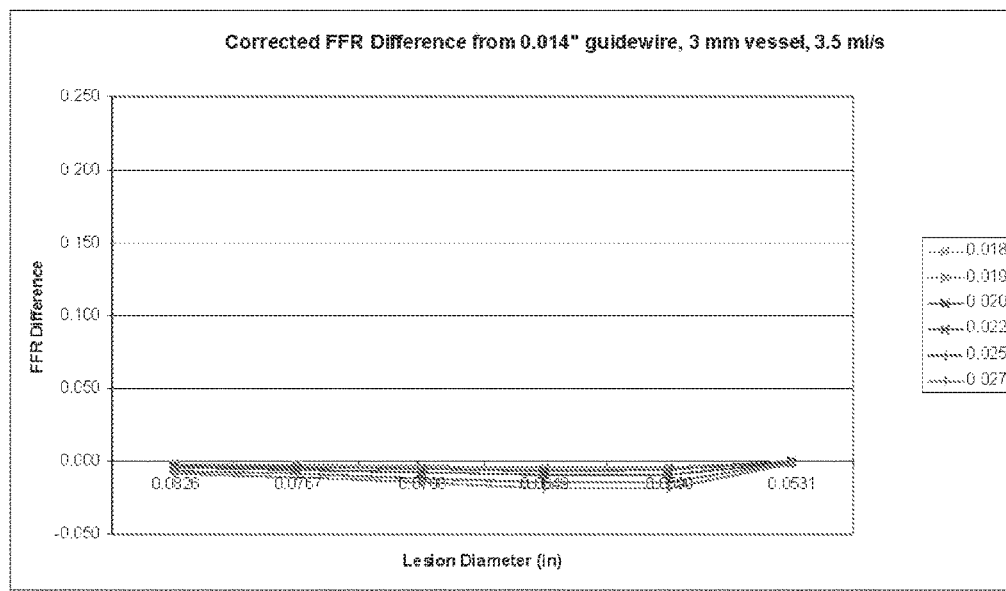
FIG. 18d is a graph of the difference between the theoretical corrected FFR values and the FFR value for a 0.014 inch pressure sensing guidewire for various devices at a blood flow rate of 3.5 ml/s.
Figure 19A:
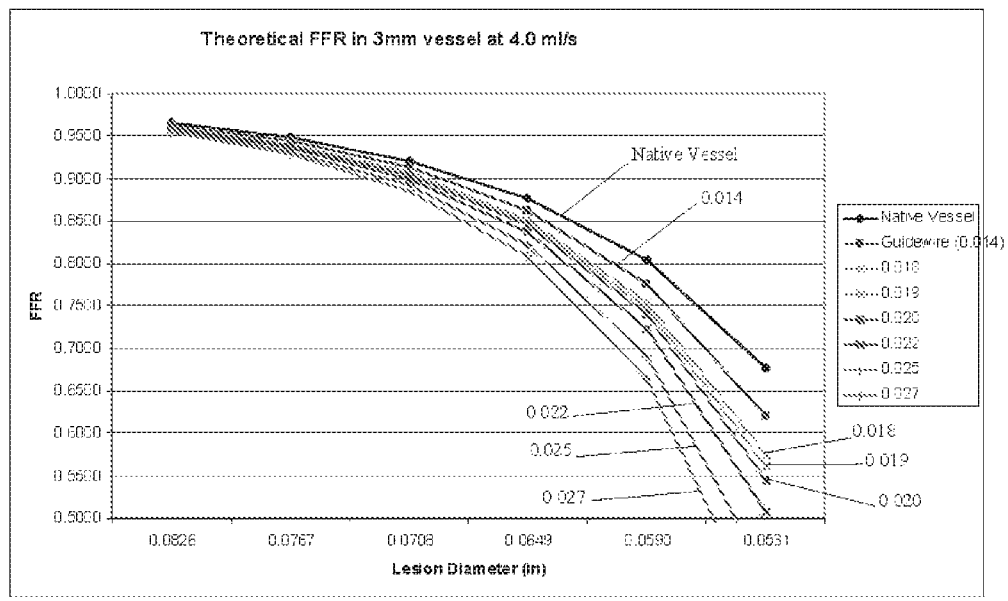
FIG. 19a is a graph of theoretical FFR values for various devices for a blood flow rate of 4.0 ml/s.
Figure 19B:
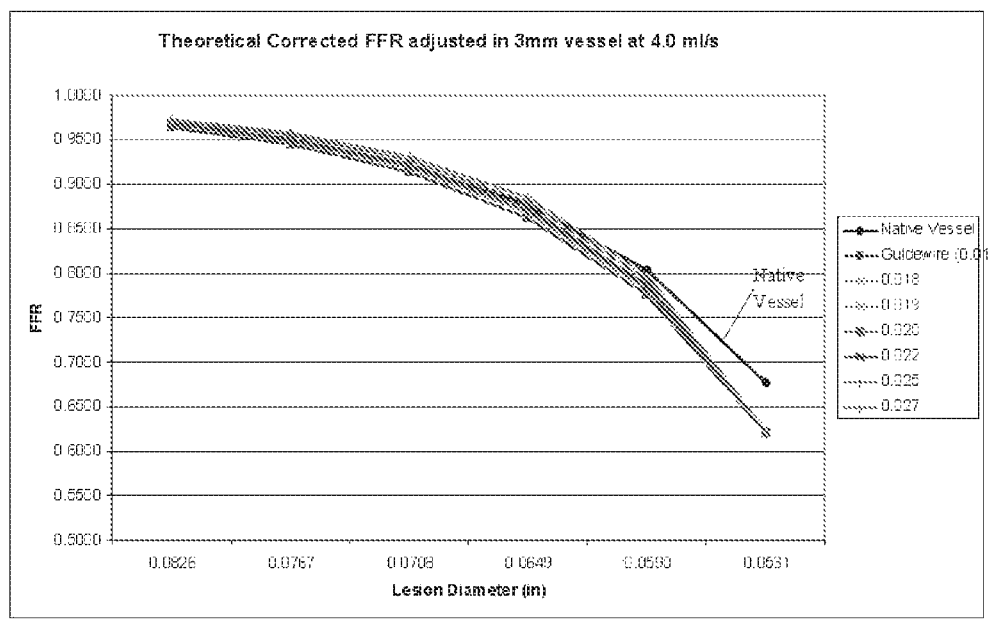
FIG. 19b is a graph of corrected theoretical FFR values for various devices for a blood flow rate of 4.0 ml/s.
Figure 19C:
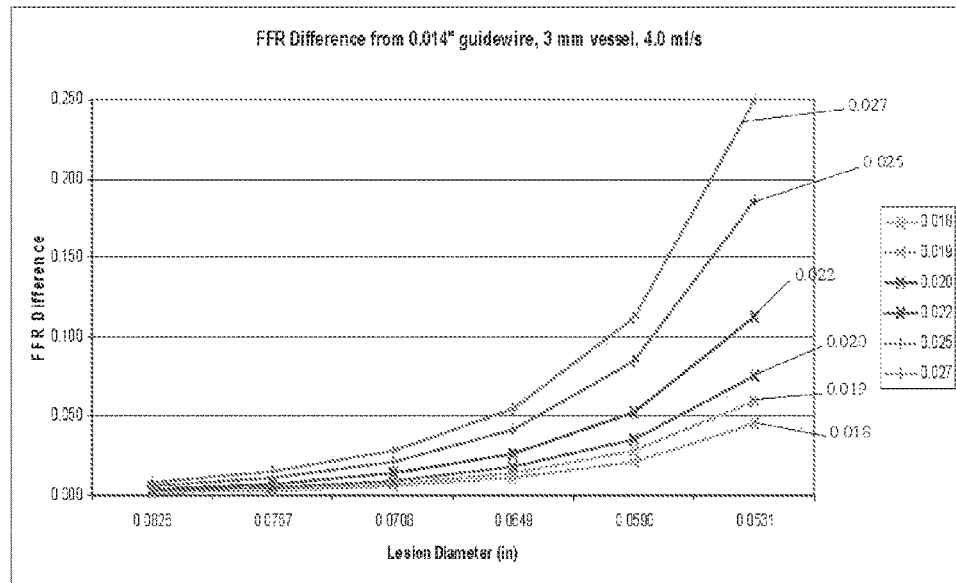
FIG. 19c is a graph of the difference between the theoretical FFR values and the FFR values for a 0.014 inch pressure sensing guidewire for various devices at a blood flow rate of 4.0 ml/s.
Figure 19D:
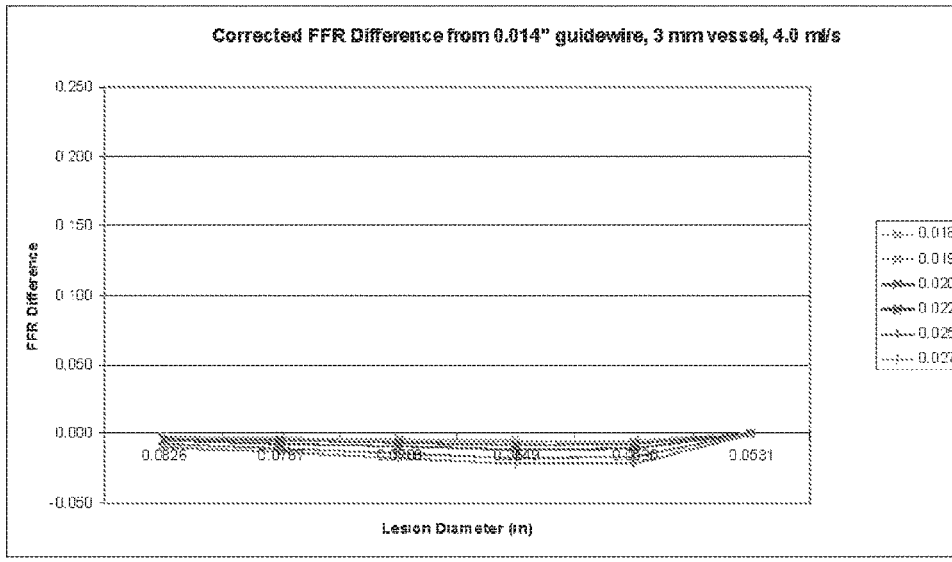
FIG. 19d is a graph of the difference between the theoretical corrected FFR values and the FFR value for a 0.014 inch pressure sensing guidewire for various devices at a blood flow rate of 4.0 ml/s.
Figure 20A:
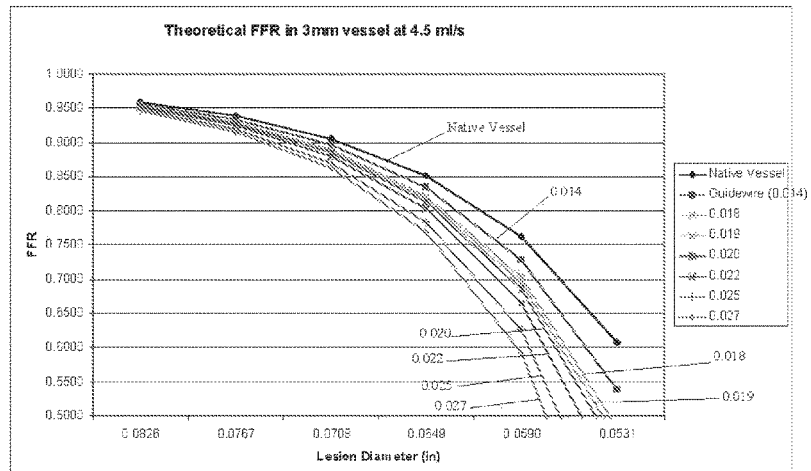
FIG. 20a is a graph of theoretical FFR values for various devices for a blood flow rate of 4.5 ml/s.
Figure 20B:
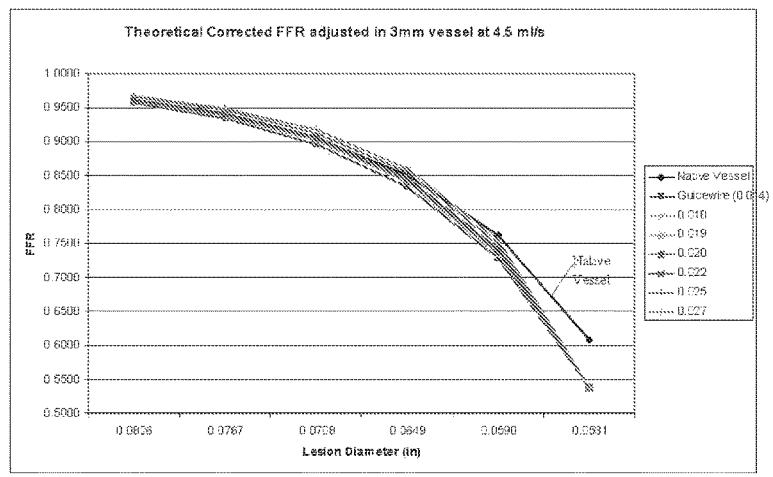
FIG. 20b is a graph of corrected theoretical FFR values for various devices for a blood flow rate of 4.5 ml/s.
Figure 20C:
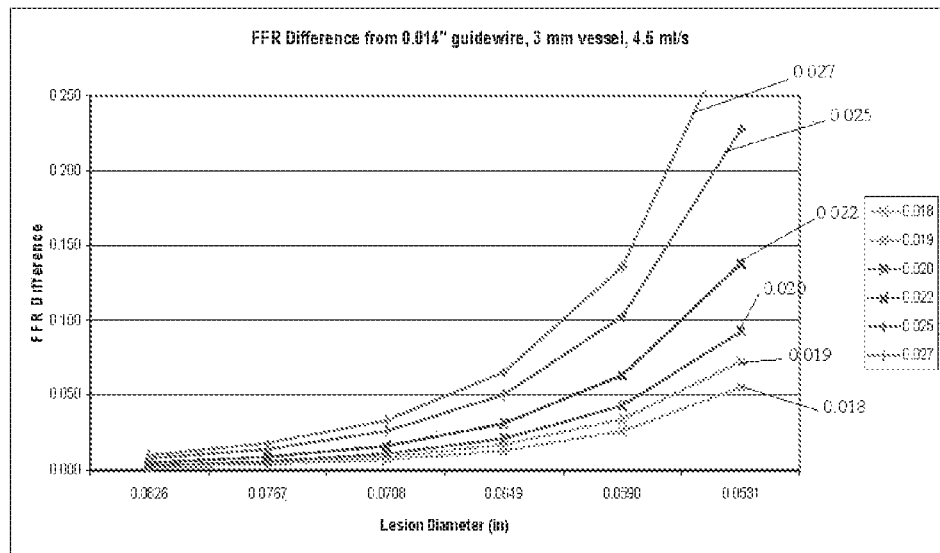
FIG. 20c is a graph of the difference between the theoretical FFR values and the FFR values for a 0.014 inch pressure sensing guidewire for various devices at a blood flow rate of 4.5 ml/s.
Figure 20D:
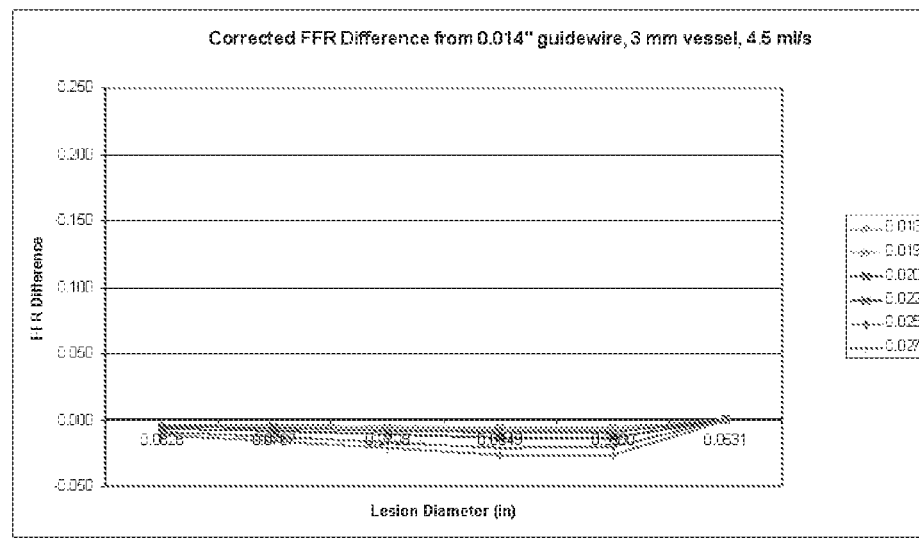
FIG. 20d is a graph of the difference between the theoretical corrected FFR values and the FFR value for a 0.014 inch pressure sensing guidewire for various devices at a blood flow rate of 4.5 ml/s.

The data from this example is further shown in FIGS. 15a, 15b, 15c, and 15d to demonstrate the effectiveness of the correction factor in correcting the calculated FFR to a corrected FFR that approximates the FFR which would be obtained using a 0.014 inch outer diameter pressure sensing guidewire. In each FIG. 15a-d, the data is for a 3 millimeter vessel and a flow rate of 2.0 ml/s, with theoretical FFR values that would be obtained in a native vessel, a 0.014 inch pressure sensing guidewire, and sensor delivery devices of 0.018, 0.019, 0.020, 0.022, 0.025, and 0.027 inches verses the lesion diameter. In FIG. 15a, the theoretical FFR values for the various sensor delivery devices are not corrected, while in FIG. 15b the theoretical FFR values were corrected using the correction factors in Table 2. Similarly in FIG. 15c the difference between the uncorrected theoretical FFR values (of FIG. 15a) and the theoretical FFR of a 0.014 inch pressure sensing guidewire are shown, while FIG. 15d shows the difference between the corrected theoretical FFR values (of FIG. 15b) for each size of sensor delivery device and the theoretical FFR for a 0.014 inch pressure sensing guidewire. The same comparison is shown in FIGS. 16a-16d for a flow rate of 2.5 ml/s, in FIGS. 17a-17d for a flow rate of 3.0 ml/s, in FIGS. 18a-18d for a flow rate of 3.5 ml/s, in FIG. 19a-19d for a flow rate of 4.0 ml/s, and in FIGS. 20a-20d for a flow rate of 4.5 ml/s. In each example, the close approximation of the corrected FFR to a FFR obtained using 0.014 inch pressure sensing guidewire that is provided by the correction factor is apparent. Similar results were also obtained for 2 mm vessel diameters and 4 mm vessel diameters (not shown), further demonstrating the usefulness of the correction factor.

Example 3

Figure 21:
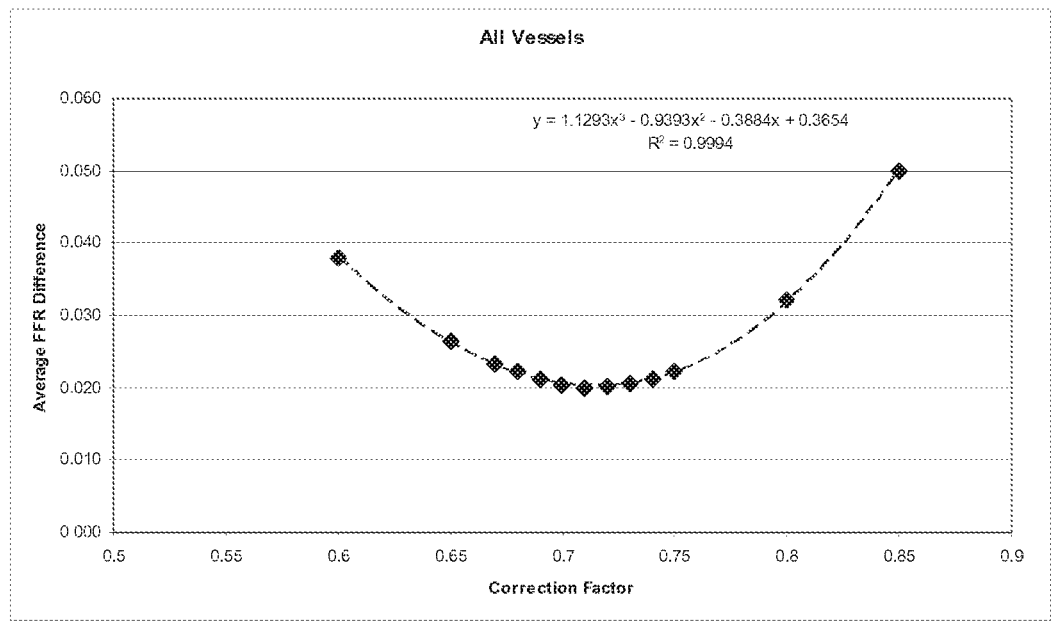
FIG. 21 is a graph of the absolute value of the difference between the theoretical corrected FFR values for a 0.022 inch device and the FFR values for a 0.014 inch pressure sensing guidewire for various correction factors for all vessel diameters.

In this example, the correction factor for a 0.022 inch monorail pressure sensing device was determined using an iterative approach. Using the theoretical calculation method described in Example 1, theoretical pressure values and FFR values were determined for a 0.022 inch outer diameter sensor delivery device using a range of flow rates and vessel sizes. Using an iterative approach, a service of possible correction factors was applied to the data to determine a corrected FFR for each measurement. The difference between the corrected FFR and the FFR for a 0.014 inch pressure sensing guidewire (the FFR difference) was determined for each possible theoretical measurement, and the absolute values of the differences were averaged for each possible correction factor. The results are shown in FIG. 21 as the average corrected FFR difference verses correction factor. The curve fit minimum represents the correction factor at which the magnitude of the FFR difference was minimized and is therefore an optimal correction factor to be used with pressure sensing devices of 0.022 inch outer diameter for all vessel sizes.

Figure 22:
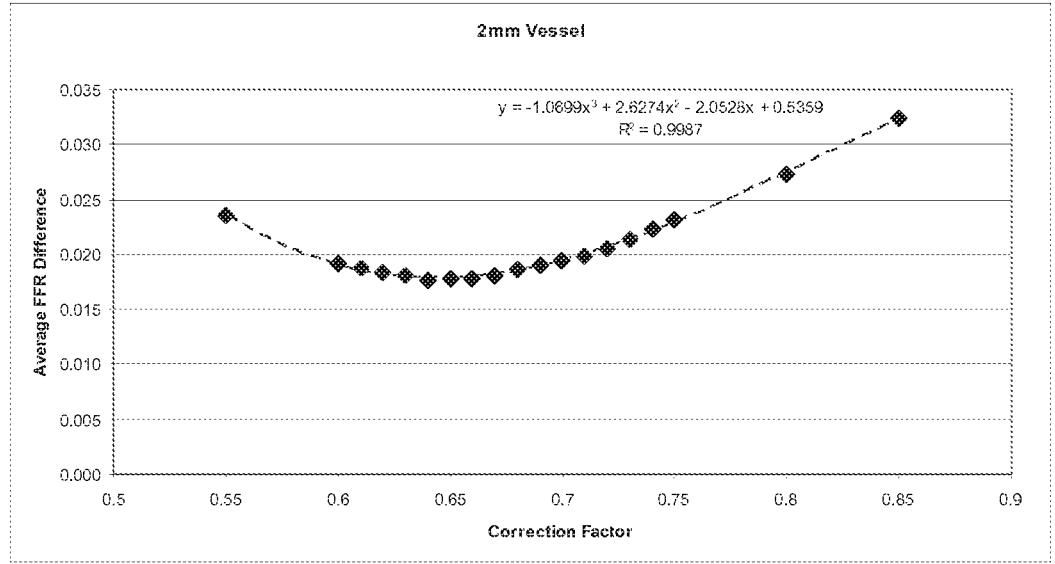
FIG. 22 is a graph of the absolute value for the difference between the theoretical corrected FFR values for a 0.022 inch device and the FFR values for a 0.014 inch pressure sensing guidewire for various correction factors for a vessel diameters of 2 mm.
Figure 23:
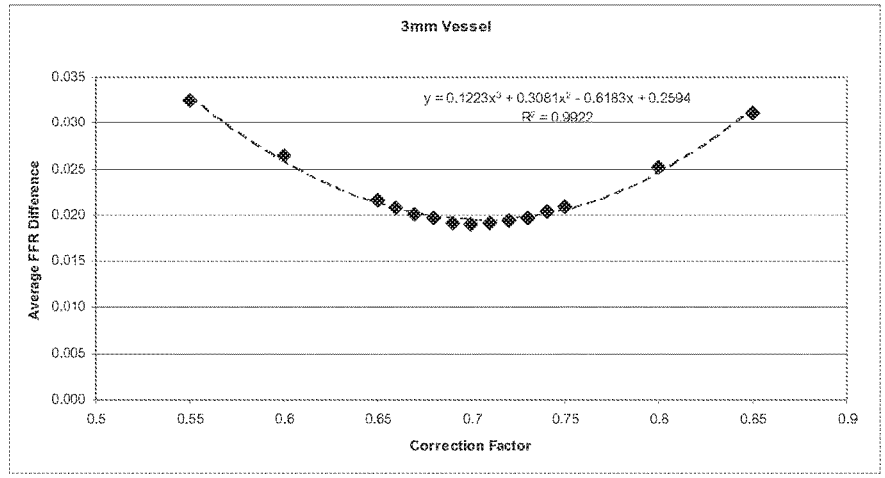
FIG. 23 is a graph of the absolute value for the difference between the theoretical corrected FFR values for a 0.022 inch device and the FFR values for a 0.014 inch pressure sensing guidewire for various correction factors for a vessel diameters of 3 mm.
Figure 24:
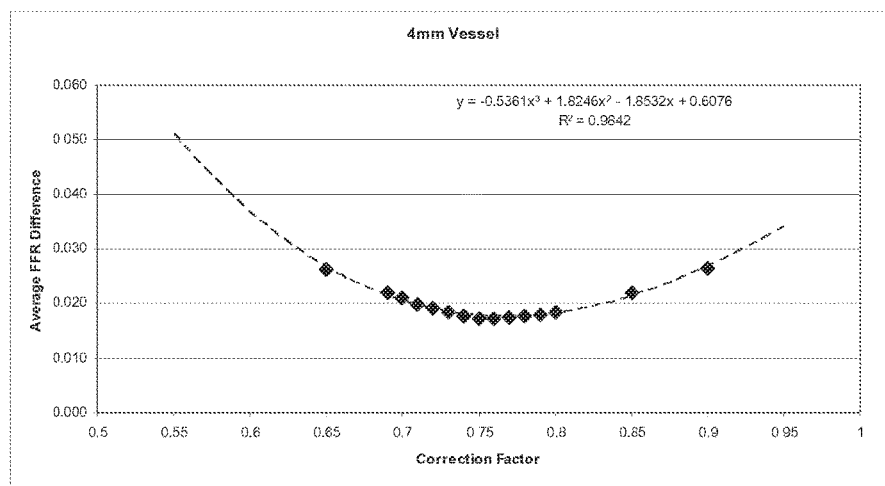
FIG. 24 is a graph of the absolute value for the difference between the theoretical corrected FFR values for a 0.022 inch device and the FFR values for a 0.014 inch pressure sensing guidewire for various correction factors for a vessel diameters of 4 mm.

The same theoretical pressure values and calculated FFR values were then segregated by vessel size to determine the correction factor for a 0.022 inch outer diameter pressure sensing device for each vessel size. A range of possible correction factors were applied to the data for a 2 mm vessel to determine a corrected FFR. The difference between the corrected FFR for 2 mm vessels and the FFR for a 0.014 inch pressure sensing guidewire for a 2 mm vessel was determined for each theoretical measurement, and the absolute values of the differences were averaged for each correction factor. The results are shown in FIG. 22 as the average FFR difference verses correction factor. The same process was performed for a 3 mm vessel in FIG. 23 and a 4 mm vessel in FIG. 24. In each case, the curve fit minimum represents the correction factor at which the magnitude of the corrected FFR difference was minimized and is therefore an optimal correction factor to be used with pressure sensing devices of 0.022 inch outer diameter for a vessel of that size. It can be seen that by using a correction factor that corresponds to both the size of the pressure sensing device (in this case, 0.022 inches) and the size of the vessel, the ability of the corrected FFR to approximate the FFR obtained using a 0.014 inch pressure sensing guidewire improves.

Figure 25:
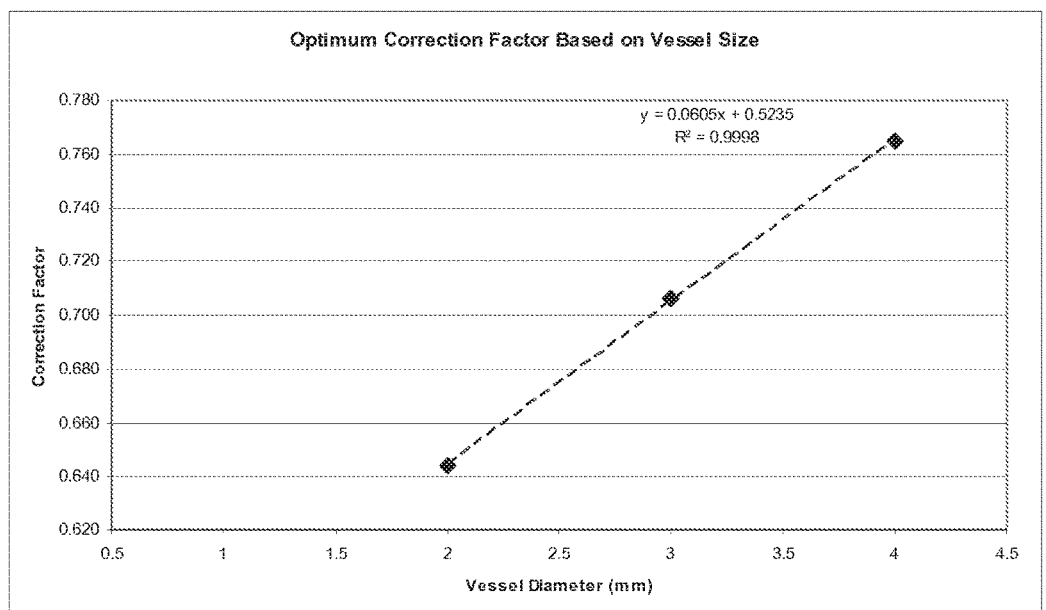
FIG. 25 is a graph of correction factor versus vessel diameter.

The optimum correction factors determined above were plotted against the corresponding vessel size in FIG. 25. A strong linear relationship was found, allowing for extrapolation of the correction factor for other vessel sizes for pressure sensing devices having an outer diameter of 0.022 inches. A similar process could be performed for other pressure sensing devices to develop a similar curve of optimum correction factors versus vessel size or any other variable for a particular size of a device.

Example 4

Figure 26:
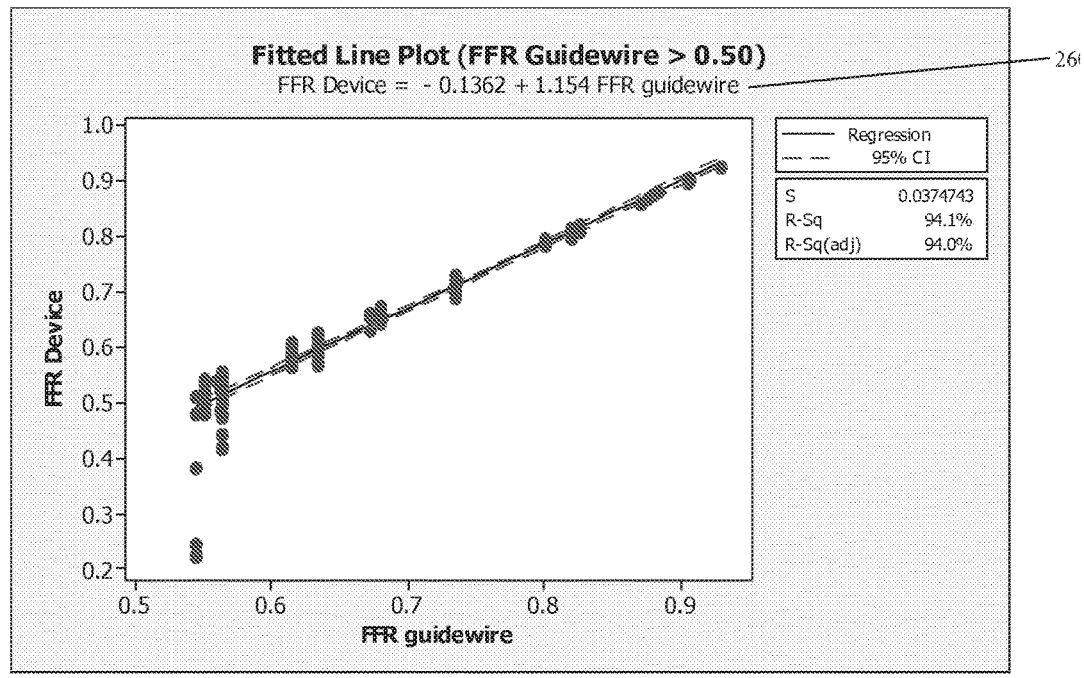
FIG. 26 is a graph of a fitted line of theoretical FFR values that would be obtained using a sensor delivery device verses FFR values that would be obtained using a guidewire sensor.
Figure 27:
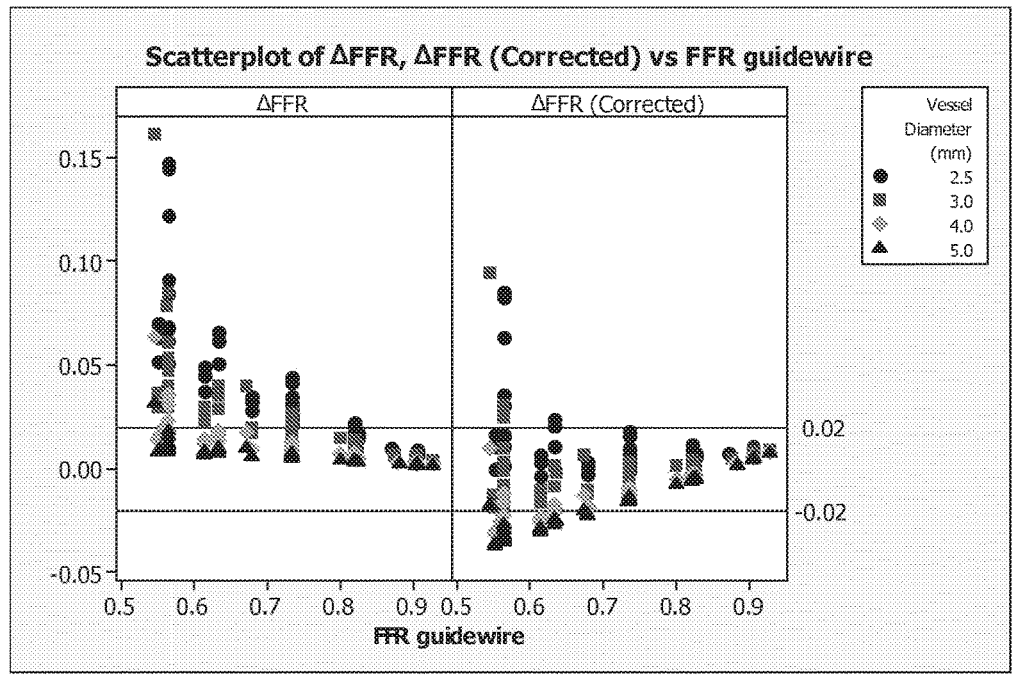
FIG. 27 is a plot of the difference between theoretical FFR values obtained using a sensor delivery device and using a guidewire sensor, and of the difference between corrected FFR values obtained using a sensor delivery device and using a guidewire sensor versus FFR obtained using the guidewire sensor.

In this example, a regression equation was developed which can be used to correct an FFR value. FIG. 26 shows a plot of theoretical calculated FFR values as measured by a device 10 (indicated as "FFR Device") versus a theoretical FFR as measured by a 0.014 inch outer diameter pressure sensing guidewire (indicated as "FFR guidewire"). A linear relationship is shown, along with the correction equation 1301 which can be used to calculate the corrected FFR, which in this case would be a correction to approximate the FFR that would be found if measurements were made with a 0.014 inch outer diameter pressure sensing guidewire. The curve fit can be calculated using a program such as Excel Curve fit functions, and in this example was done using Minitab® Regression Analysis. In FIG. 27, the difference between the theoretical calculated FFR using the device 10 and the theoretical FFR using the pressure sensing guidewire is shown as ΔFFR in the left side of the plot. As a comparison, in the right side, the theoretical calculated FFR using the device 10 was corrected using correction equation 2601 to determine $FFR_{corr}$, and $\Delta FFR_{corr}$ represents the difference between $FFR_{corr}$ and the FFR using the 0.014 pressure sensing guidewire. It can be seen that the correction equation 2601 can correct the calculated FFR to approximate the FFR that would be obtained if the pressure measurements were made with a pressure sensing guidewire.

The foregoing description addresses examples encompassing the principles of various embodiments of the present invention. The embodiments may be changed, modified and/or implemented using various types of arrangements. Those skilled in the art will readily recognize various modifications and changes that may be made to these embodiments of the invention without strictly following the exemplary embodiments and applications illustrated and described herein, and without departing from the scope of the invention. Accordingly, it is not intended that the invention be limited, except as by the appended claims.

The invention claimed is:

1. A method of calculating a corrected Fractional Flow Reserve (FFR) using a first pressure sensing device at a location in a blood vessel having a stenosis, the first pressure sensing device having a pressure sensor, the method comprising:

measuring a pressure downstream of the stenosis with the first pressure sensing device while the pressure sensor is positioned downstream of the stenosis, the first pressure sensing device having a first maximum cross-sectional area in a distal portion of the first pressure sensing device;

measuring a pressure upstream of the stenosis;

calculating with a processing device a corrected FFR using the measured upstream and downstream pressures and applying a correction factor or correction equation;

wherein the correction factor or correction equation corrects for errors in the pressure measured downstream of the stenosis caused by the presence of the first pressure sensing device; and wherein the corrected FFR approximates a FFR that would have been obtained if the pressure measured downstream of the stenosis was measured using a second pressure sensing device having a second maximum cross-sectional area in a distal portion of the second pressure sensing device that is different from the first maximum cross-sectional area, the correction factor or correction equation accounting for the second maximum cross-sectional area.

2. The method of claim 1, further comprising selecting the correction factor or correction equation from a group of at least two correction factors or correction equations, wherein the selection of the correction factor or correction equation corresponds to the cross-sectional area of the first pressure sensing device, or by a type of the first pressure sensing device.

3. The method of claim 2, wherein the selection of the correction factor or correction equation is further determined by one or more of a size of the stenosis, a size of a lumen of the blood vessel, and a rate of blood flow.

4. The method of claim 3, wherein the first pressure sensing device comprises one or more sensors configured to measure the size of the stenosis, the size of the lumen, and/or the rate of blood flow.

5. The method of claim 1, wherein the second pressure sensing device is a pressure sensing guidewire and/or the distal portion of the second pressure sensing device has a maximum diameter of about 0.014 inches.

6. The method of claim 1, wherein calculating the corrected FFR comprises applying the correction factor to the measured downstream pressure to get a corrected downstream pressure, and calculating the corrected FFR using the corrected downstream pressure.

7. The method of claim 1, wherein calculating the corrected FFR comprises calculating a measured FFR using the measured downstream pressure, and applying the correction equation to the measured FFR to calculate the corrected FFR.

8. The method of claim 1, further comprising displaying the corrected FFR on a visual display.

9. A system for calculating a corrected Fractional Flow Reserve (FFR) associated with a stenosis in a blood vessel, the system comprising:

a first pressure sensing device configured for placement within the blood vessel to measure pressure within the blood vessel downstream of the stenosis, the first pressure sensing device having a first maximum cross-sectional area in a distal portion of the first pressure sensing device;

a processing device in communication with the first pressure sensing device; and a correction factor or correction equation accounting for the first maximum cross-sectional area, wherein the correction factor or correction equation is stored within a memory component of the processing device or within a memory component accessible by the processing device;

wherein the processing device is configured to calculate a corrected FFR using the correction factor or correction equation and the pressure measured downstream of the stenosis by the first pressure sensing device; and wherein the corrected FFR approximates a FFR that would have been obtained if the pressure measured downstream of the stenosis was measured using a second pressure sensing device having a second maximum cross-sectional area in a distal portion of the second pressure sensing device that is different from the first maximum cross-sectional area, the correction factor or correction equation accounting for the second maximum cross-sectional area.

10. The system of claim 9, wherein the second pressure sensing device is a pressure sensing guidewire and/or the distal portion of the second pressure sensing device has a maximum diameter of about 0.014 inches.

11. The system of claim 9, wherein the first pressure sensing device comprises one or more sensors configured to measure at least one of a size of the stenosis, a size of a lumen, a rate of blood flow, or any combination thereof.

12. The system of claim 9, wherein the selection of the correction factor or correction equation is further determined by one or more of the size of the stenosis, the size of a lumen of the vessel, a rate of blood flow, or any combination thereof.

13. The system of claim 9, wherein the processing device configured to calculate the corrected FFR is configured to apply the correction factor to the measured downstream pressure to calculate a corrected downstream pressure, and use the corrected downstream pressure to calculate the corrected FFR.

14. The system of claim 9, wherein the processing device is configured to calculate a measured FFR using the measured downstream pressure, and to calculate the corrected FFR by applying the correction equation to the measured FFR to calculate the corrected FFR.

15. A method of calculating a corrected Fractional Flow Reserve (FFR) using a first pressure sensing device at a location in a blood vessel having a stenosis, the first pressure sensing device having a pressure sensor, the method comprising:

measuring a pressure downstream of the stenosis with the first pressure sensing device while the pressure sensor is positioned downstream of the stenosis, the first pressure sensing device having a first maximum cross-sectional area in a distal portion of the first pressure sensing device;

measuring a pressure upstream of the stenosis;

calculating with a processing device a corrected FFR using the measured upstream and downstream pressures and applying a correction factor or correction equation;

wherein the correction factor or correction equation is stored within a memory component of the processing device or within a memory component accessible by the processing device, and wherein the correction factor or correction equation accounts for the first maximum cross-sectional area; and wherein the corrected FFR approximates a FFR that would have been obtained if the pressure measured downstream of the stenosis was measured using a second pressure sensing device having a second maximum cross-sectional area in a distal portion of the second pressure sensing device that is different from the first maximum cross-sectional area, the correction factor or correction equation accounting for the second maximum cross-sectional area.

16. The method of claim 15, wherein the second pressure sensing device is a pressure sensing guidewire, and/or the distal portion of the second pressure sensing device has a maximum diameter of about 0.014 inches.

17. The method of claim 15, further comprising selecting the correction factor or correction equation from a group of at least two correction factors or correction equations, wherein the selection of the correction factor or correction equation corresponds to the maximum cross-sectional area of the first pressure sensing device in the distal portion of the device, or by a type of the first pressure sensing device.

18. The method of claim 15, wherein the selection of the correction factor or correction equation is further determined by one or more of a size of the stenosis, a size of a lumen of the blood vessel, and a rate of blood flow.

19. The method of claim 15, wherein calculating the corrected FFR comprises applying the correction factor to the measured downstream pressure to get a corrected downstream pressure, and calculating the corrected FFR using the corrected downstream pressure.

20. The method of claim 15, wherein calculating the corrected FFR comprises calculating a measured FFR using the measured downstream pressure, and applying the correction equation to the measured FFR to calculate the corrected FFR.

* * * * *